(12) United States Patent
Iyer et al.

(10) Patent No.: US 9,132,099 B2
(45) Date of Patent: Sep. 15, 2015

(54) MEDICAL IMPLANTS AND METHODS FOR REGULATING THE TISSUE RESPONSE TO VASCULAR CLOSURE DEVICES

(71) Applicant: Vascular Therapies LLC, New York, NY (US)

(72) Inventors: Sriram Iyer, New York, NY (US); Nicholas Kipshidze, New York, NY (US); Victor Nikolaychik, Thiensville, WI (US); Gary Roubin, Jackson, WY (US)

(73) Assignee: VASCULAR THERAPIES, INC., Cresskill, NJ (US)

( * ) Notice: Subject to any disclaimer, the term of this patent is extended or adjusted under 35 U.S.C. 154(b) by 0 days.

(21) Appl. No.: 13/845,387

(22) Filed: Mar. 18, 2013

(65) Prior Publication Data
US 2014/0065198 A1     Mar. 6, 2014

Related U.S. Application Data

(63) Continuation of application No. 10/871,902, filed on Jun. 18, 2004, now abandoned, which is a continuation-in-part of application No. 10/765,005, filed on Jan. 26, 2004, now abandoned, which is a continuation of application No. 10/431,737, filed on May 8, 2003, which is a continuation of application No. 10/051,708, filed on Jan. 16, 2002, now Pat. No. 6,726,923.

(60) Provisional application No. 60/262,132, filed on Jan. 16, 2001, provisional application No. 60/479,789, filed on Jun. 19, 2003.

(51) Int. Cl.
*A61L 15/16* (2006.01)
*A61F 13/00* (2006.01)
*A61F 2/00* (2006.01)
*A61K 38/00* (2006.01)
*A61K 38/13* (2006.01)
*A61K 31/727* (2006.01)
*A61K 9/70* (2006.01)
*A61B 17/00* (2006.01)
*A61K 31/436* (2006.01)
*A61K 31/4745* (2006.01)
*A61L 31/04* (2006.01)
*A61L 31/16* (2006.01)

(52) U.S. Cl.
CPC .......... *A61K 9/7007* (2013.01); *A61B 17/0057* (2013.01); *A61K 31/436* (2013.01); *A61K 31/4745* (2013.01); *A61L 31/044* (2013.01); *A61L 31/16* (2013.01); *A61B 2017/00641* (2013.01); *A61B 2017/00659* (2013.01); *A61B 2017/00893* (2013.01); *A61L 2300/416* (2013.01)

(58) Field of Classification Search
None
See application file for complete search history.

*Primary Examiner* — Jeffrey T Palenik
(74) *Attorney, Agent, or Firm* — Mayer Brown LLP

(57) ABSTRACT

Devices and methods for reducing, eliminating, preventing, suppressing, or treating tissue responses to hemostatic devices e.g., biological sealants or vascular procedures are disclosed. The invention employs a combination of resorbable, biocompatible matrix materials and a variety of therapeutic agents, such as antiproliferatives or antibiotics, applied to a vascular puncture or incision to achieve hemostasis following diagnostic or interventional vascular catheterizations and to treat neointimal hyperplasia and stenosis. A matrix of a material such as collagen provides a reservoir of a therapeutic agent such as rapamycin (sirolimus) and its derivatives and analogs for delivery at a tissue site at risk for vasculoproliferation, infection, inflammation, fibrosis or other tissue responses.

33 Claims, 17 Drawing Sheets

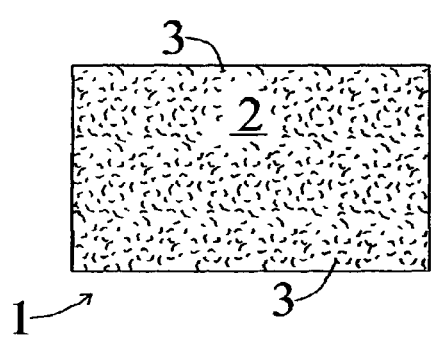
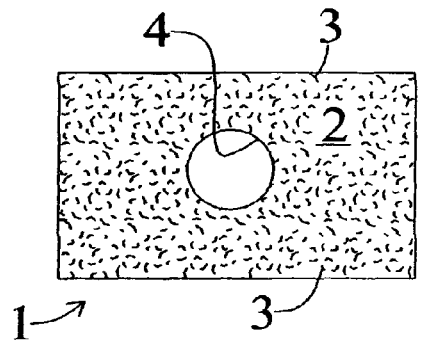
FIG. 1A   FIG. 1B
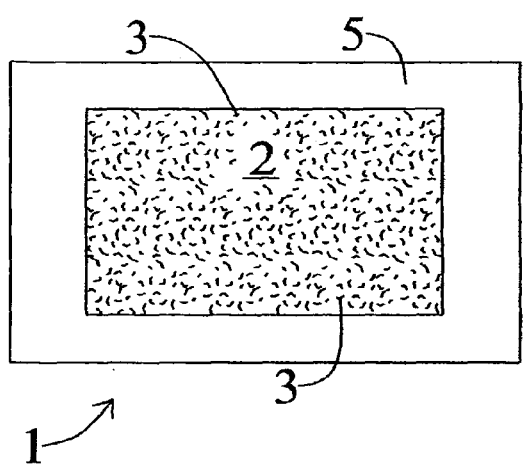
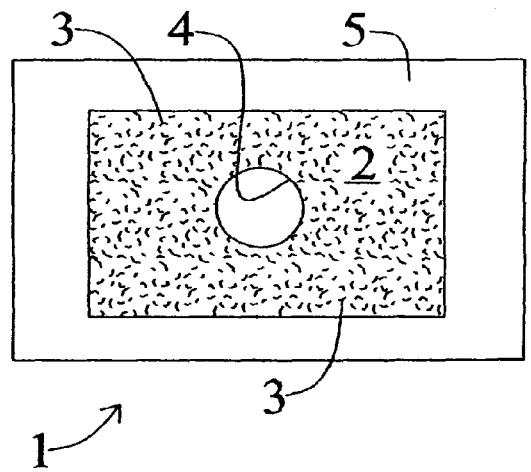
FIG. 2A   FIG. 2B

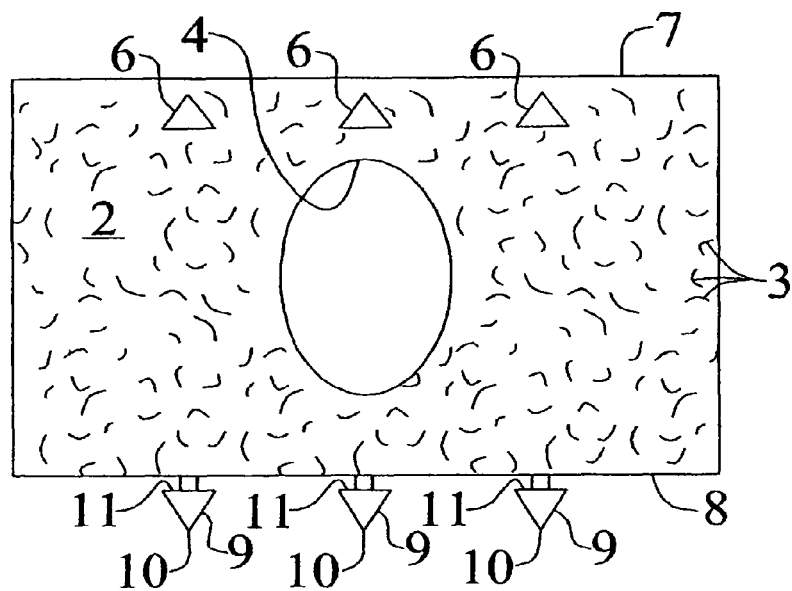
FIG. 3A
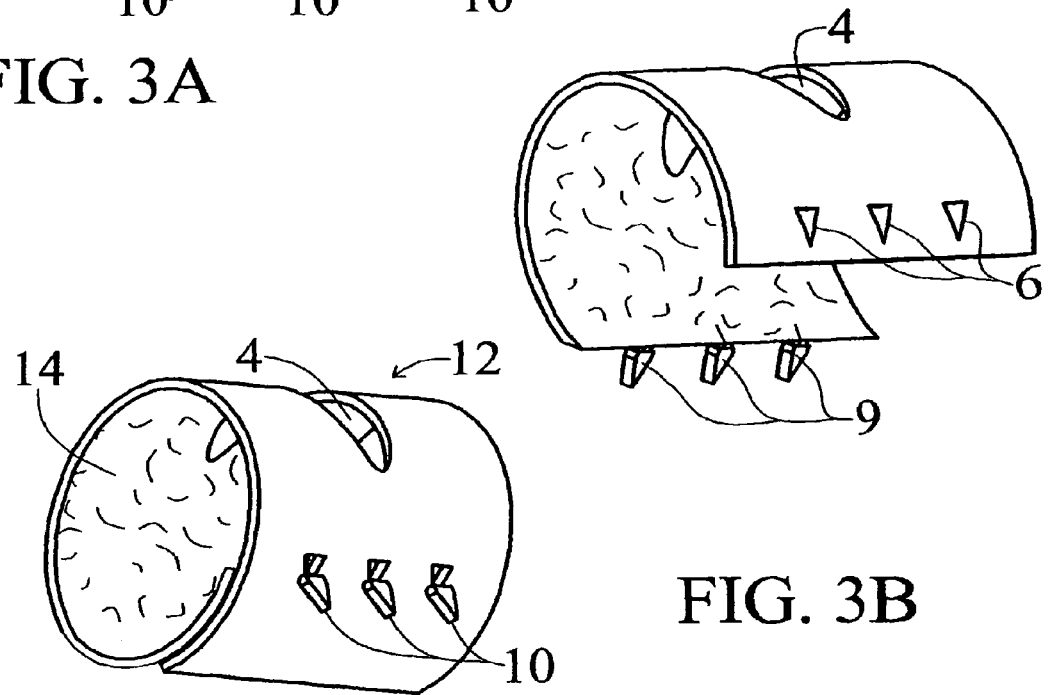
FIG. 3B
FIG. 3C

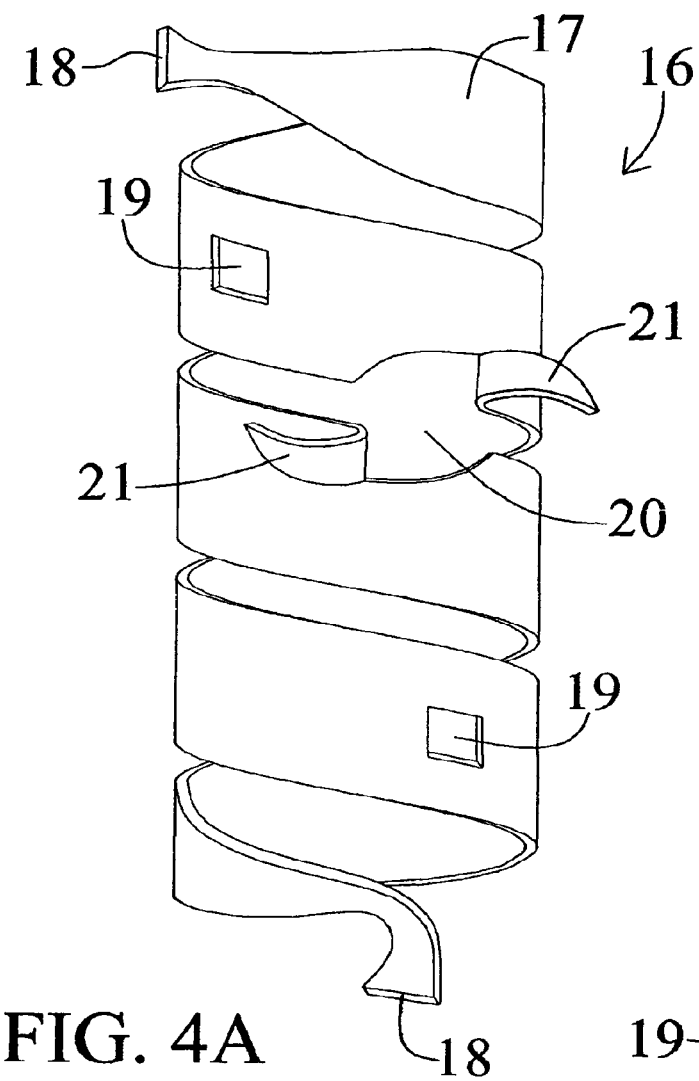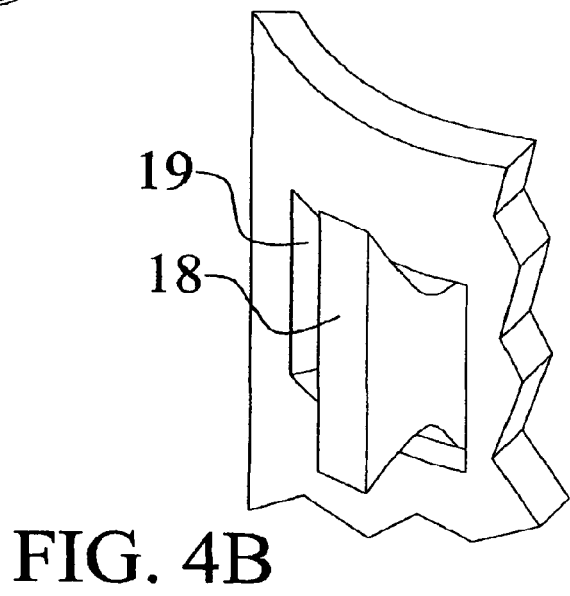
FIG. 4A
FIG. 4B

FIG. 12
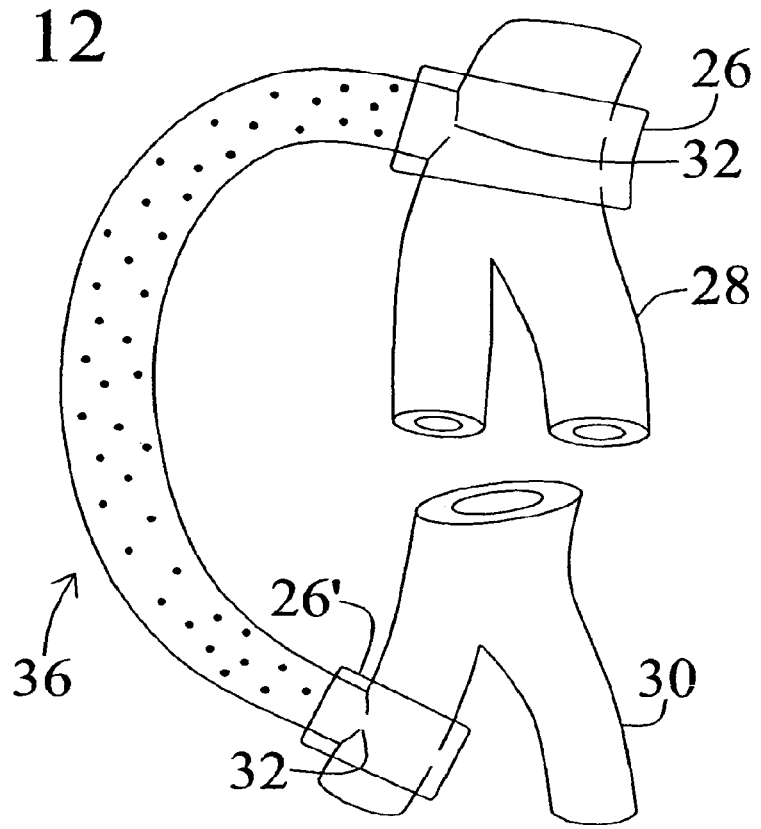
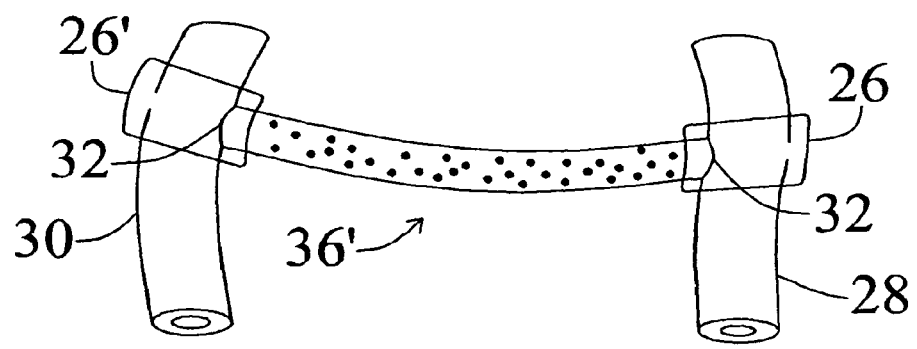
FIG. 13

Four Week Follow Up Angiograms

CONTROL 238　　　　　　TREATED 241

Arrow with circle on tail indicate site of anastamosis

Histo – Pathology at 4 weeks

CONTROL 238

TREATED 241

Region Between small arrows indicates thickness of neointima

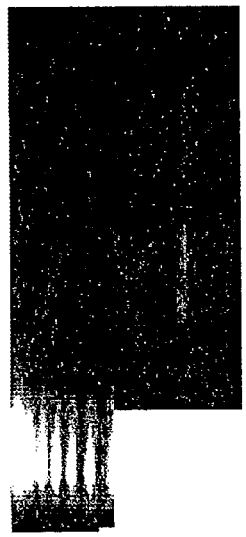

MEDICAL IMPLANTS AND METHODS FOR REGULATING THE TISSUE RESPONSE TO VASCULAR CLOSURE DEVICES

RELATED APPLICATIONS

This is a continuation application of U.S. patent application Ser. No. 10/871,902 filed on Jun. 18, 2004, which is a continuation-in-part application of U.S. patent application Ser. No. 10/765,005 filed Jan. 26, 2004, which is a continuation of U.S. patent application Ser. No. 10/431,737 filed on May 8, 2003, which is a continuation of U.S. patent application Ser. No. 10/051,708 filed on Jan. 16, 2002, now U.S. Pat. No. 6,726,923, which claimed priority to U.S. Provisional Patent Application Ser. No. 60/262,132 filed on Jan. 16, 2001. This application further claims priority to U.S. Provisional Patent Application Ser. No. 60/479,789 filed Jun. 19, 2003. All such applications are incorporated herein by reference to the extent permitted by law.

BACKGROUND

The present invention relates generally to therapeutic implants, devices, and methods useful for preventing, suppressing, or treating failure of hemodialysis vascular access grafts and other vascular procedures. The invention also relates to therapeutic implants comprising a matrix material and a therapeutic agent, wherein the composition placed in external contact with a blood vessel (perivascular implant of the composition) can be used to achieve hemostasis, e.g., to seal a breach in the vascular wall and to deliver a therapeutic agent capable of regulating the amount of tissue response to the implanted matrix.

Vascular procedures such as construction of hemodialysis access grafts and angioplasty are performed to provide vascular access in patients with renal failure in need of hemodialysis dysfunction and treat conditions such as atherosclerosis. Hemodialysis vascular access grafts can be constructed as an arterio-venous fistula (e.g., Brecisa-Cimino), or as a graft interposing either prosthetic material (e.g., polytetrafluoroethylene "PTFE") or biological tissue (e.g., vein) between an artery and a vein.

Such grafts are usually constructed using a tubular or cylindrical segment of suitably biocompatible and substantially inert material such as PTFE, the most common material used for prosthetic dialysis access. In one approach, a segment of PTFE is surgically interposed between an artery and a vein in the arm, forearm, or thigh. The graft is then available for repeated vascular access in performing hemodialysis.

Subsequent to placement of the graft, the sutured sites in the artery and the vein undergo healing. However, 60 percent of these grafts fail, usually because of luminal narrowing, or stenosis, at the venous end. Similar lesions develop in synthetic PTFE grafts placed in the arterial circulation, although stenosis in arterial grafts develops slower than at venous ends. Failure or dysfunction of grafts used in coronary artery bypass surgery or peripheral vascular surgery (e.g., aortailiac, femoral-femoral, femoral-popliteal, femoral tibial) is well known. Failure of vascular grafts or arterial reconstruction results from luminal narrowing of the vessel or prosthetic conduit, at or away from the anastamotic site, from intraluminal thrombus or a vasculoproliferative response, or from other pathologies, for example, infection of the prosthetic graft.

Neointimal hyperplasia, a manifestation of the vasculoproliferative response, affects the vessel and adjacent graft orifice. The vessel wall thickens and the lumen narrows due to migration and proliferation of smooth muscle cells. The etiology of graft failures may relate to a variety of physical (e.g., shear stress causing hemodynamic disturbance), chemical, or biological stimuli, as well as infection or foreign body rejection, which may explain why fistulae that do not involve a foreign body (e.g., PTFE) remain patent longer than vascular access grafts that involve interposition of a PTFE graft. As the stenosis in the graft becomes progressively more severe, the graft becomes dysfunctional and access for medical procedures suboptimal. Left untreated, stenosis eventually leads to occlusion and graft failure.

The venous ends of grafts are prone to narrowing for multiple reasons. This location is uniquely exposed to arterial pressures and arterial flow rates, dissipation of acoustic or vibratory energy in the vessel wall and surrounding tissue, repeated puncture of the graft, and infusion of processed blood. In addition, in the hemodialysis example, the venous end of the graft may be bathed in mitogens released during passage of the blood through the dialysis tubing or during activation of platelets at the site of needle puncture.

Tissue samples collected from the graft-vein anastomosis site of stenotic PTFE grafts during surgical revision show significant narrowing of the lumen and are characterized by the presence of smooth muscle cells, accumulation of extracellular matrix, angiogenesis within the neointima and adventitia, and presence of an active macrophage cell layer lining the PTFE graft material. A large variety of cytokines and cell growth stimulating factors like platelet-derived growth factor (PDGF), basic fibroblast growth factor (bFGF), and vascular endothelial growth factor (VEGF) are expressed by smooth muscle cells or myofibroblasts within the venous neointima, macrophages lining both sides of the PTFE graft, and vessels within the neointima and adventitia. Macrophages, specific cytokines (PDGF, bFGF, and VEGF), and angiogenesis within the neointima and adventitia have been suggested as likely contributing to the pathogenesis of venous neointimal hyperplasia.

In the hemodialysis example, venous neointimal hyperplasia characterized by stenosis and subsequent thrombosis accounts for the overwhelming majority of pathology resulting in PTFE dialysis graft failure, which prevents hemodialysis, leading to renal failure, clinical deterioration, and death. Vascular access dysfunction is the most important cause of morbidity and hospitalization in the hemodialysis population. Despite the magnitude of the problem and associated costs, however, no effective therapies currently exist for the prevention or treatment of venous neointimal hyperplasia in PTFE dialysis grafts.

Once stenosis has occurred, the treatment consists of further vascular reconstruction. One current method of treatment involves reduction or obliteration of the narrowing and restoration of bloodflow through the graft by non-surgical, percutaneous catheter-based treatments such as balloon angioplasty. This procedure involves deploying a balloon catheter at the site of the blockage and inflating the balloon to increase the minimum luminal diameter of the vessel by compressing the material causing the restriction against the interior of the vessel wall. Depending upon the length and severity of the restriction, the procedure may be repeated several times by inflating and deflating the balloon. When completed, the balloon catheter is withdrawn from the system.

Although balloon angioplasty can be used as a "stand alone" procedure, it is frequently accompanied by deployment of a stent. A stent is an expandable scaffolding or support device that is placed within the vasculature to prevent mechanical recoil and to reduce the chance of renarrowing, or restenosis, at the site of the original restriction. Stents are either "balloon-expandable" or "self-expanding" and when deployed endovascularly, abut against the inner vessel wall. Whether or not a stent is placed, this form of treatment has a high risk of failure, i.e., a high risk of restenosis at the treatment site. Unless stenosis can be effectively and permanently treated, graft failure tends to follow.

In the event of graft failure, the patient must undergo an endovascular procedure, i.e., a non-surgical, catheter-based percutaneous procedure or repeat vascular surgery such as thrombectomy to "declot" the graft or to place another vascular access graft or a shunt at a different site, unless the patient receives a kidney transplant. Given the obvious problems of repeat surgeries and the limited availability of transplants, treatment that is both effective and durable in preventing and treating stenosis is needed.

The vast majority of current approaches for treating the vasculoproliferative response believed to be the pathophysiological basis of stenosis and restenosis is based on treating from within the vascular or graft lumen. One current approach utilizes drug-coated or drug-impregnated stents that are deployed within the lumen of the vessel. Examples of drugs used to coat stents include rapamycin (sirolimus or Rapamune®) commercially available from Wyeth (Collegeville, Pa.) and paclitaxel (Taxol®) commercially available from Bristol-Myers Squibb Co. (New York, N.Y.). In this stent-based approach, rapamycin or paclitaxel gradually elutes from the stent and diffuses into the vessel wall from the intima, the innermost layer of the vessel wall, to the adventitia, the outermost layer of the vessel wall. Studies have shown that rapamycin and paclitaxel tend to inhibit smooth muscle cell proliferation.

Delivery of drugs from the perivascular or extravascular space through the vascular wall, by utilizing a synthetic matrix material (ethylene-vinyl acetate copolymer) together with an anticoagulant that also has antiproliferative properties, e.g., heparin, has been suggested. However, this approach has two disadvantages. Heparin is soluble and rapidly disappears from the vascular wall, and ethylene-vinyl acetate copolymer is not biodegradable, potentially raising concerns about long term effects in vivo.

To effectively deliver a therapeutic agent locally using a matrix material-based system, the matrix material should preferably have certain characteristics. The matrix material should permit the loading of adequate quantity of the therapeutic agent. The matrix material should elute the therapeutic agent at an appropriate, well-defined rate. The matrix material should preferably be implantable and biodegradable, so as to not require physical removal of the matrix material from the recipient's tissue following drug delivery and to obviate concerns about long term effects of the residual matrix.

Furthermore, the matrix material and its biodegradation products should not provoke a significant inflammatory or proliferative tissue response and should not alter or interfere with the recipient's natural defense systems or healing. The device comprising the matrix material and the therapeutic agent should be flexible enough to mould to the contours of the vasculature. The device should also be amenable to being fixed in place, such that it does not migrate to an unintended location.

Polymer matrix materials used for drug delivery within the context of implantable devices can be either natural or synthetic. Examples include but are not limited to polymers composed of chemical substances like polyglycolic acid, polyhydroxybutyrate, ethylene-vinyl acetate, or natural polymers like collagen and fibrin, or polysaccharides such as chitosan. Matrix materials with poor mechanical characteristics, potential immunogenicity, toxic degradation products, inflammatory properties, or a tendency to induce a proliferative response would be inappropriate.

A well-known biocompatible, biodegradable, resorbable matrix material for drug delivery is collagen. The use of collagen as a material for fabrication of biodegradable medical devices has undergone serious scrutiny (U.S. Pat. Nos. 6,323,184; 6,206,931; 4,164,559; 4,409,332; 6,162,247). One current approach using collagen involves delivery of pharmaceutical agents, including antibiotics and physiologically active proteins and peptides such as growth factors. Effective delivery of any therapeutic agent should also preferably not interfere with the natural healing process.

SUMMARY OF THE INVENTION

The present invention relates to devices and methods for preventing, suppressing, or treating the vasculoproliferative response to vascular procedures or devices. In one embodiment, the invention prevents, suppresses, or treats vasculoproliferative disease by delivering one or more therapeutic agents from outside the vasculature and through the vascular wall. The invention may be advantageously used before stenosis has occurred or to treat established neointimal hyperplasia, or to prevent fibrous tissue after incisions.

Another aspect of this invention is directed to methods for reducing, eliminating or prophylactically treating the tissue response that accompanies the perivascular placement of a synthetic or biological matrix (e.g., collagen), suture, staple, clip or other form of prosthetic device for sealing the punctures in blood vessels, (artery or vein). Such matrices referred to as vascular closure devices are typically used to achieve hemostasis at point(s) of entry into the vascular system such as those that occur following percutaneous diagnostic and interventional cardiac, carotid and peripheral vascular catheterizations.

Although the perivascular placement of the matrix (e.g., collagen matrix) is effective in sealing the point of vascular wall breach thereby achieving hemostasis, the biodegradable collagen matrix can provoke tissue response(s) that can potentially envelop the blood vessel at the site of placement of the matrix. Such tissue response(s) may increase the morbidity of the vascular closure device, may render palpation of the arterial pulse (a helpful clinical pre-requisite for obtaining future vascular access) more difficult and make future percutaneous access at or through the placement of such matrices more difficult. By combining a therapeutic agent or agents to the collagen matrix, it is an object of the present invention to provide a method and a composition for reducing the host response to the perivascular collagen matrix vascular sealant applied to the wall of an arterial or venous puncture site.

One embodiment of the invention comprises a device composed of a resorbable, biocompatible matrix combined with at least one therapeutic agent. The device may optionally further comprise pharmaceutically acceptable adjuvants or additives. The device may be placed on the outer surface of a vessel to elute a tissue response regulating amount of a therapeutic agent, such as an agent that inhibits smooth muscle cell proliferation. The biocompatible matrix creates a reservoir of the therapeutic agent and controls the delivery kinetics.

In one embodiment, the biocompatible matrix is a biodegradable layer of collagen, with an optional exterior support structure or layer of PTFE and imbibed with one or more therapeutic agents, such as rapamycin. This therapeutic agent imbibed matrix may be made more adhesive to the vascular wall by combining the matrix with fibrin sealant, acetylated collagen, or photoreactive groups that can be stimulated by ultraviolet light.

Yet another aspect of the present invention comprises a method for reducing, eliminating or prophylactically treating the host response to the perivascularly applied collagen matrix (sealant) or hemostatic device. The hemostatic device may be biological, polymer based or mechanical. When placed at a site of vascular puncture or incision, the matrix, besides functioning as a sealant at the site of the vascular pucture site, incision site or site of vascular breach, allows for gradual elution of the therapeutic agent and serves as an extravascular source of drug delivery. Elution of the therapeutic agent such as rapamycin into and through the vascular wall occurs during the healing of anastamotic sites to prevent, suppress, or treat smooth muscle cell proliferation or other tissue responses to the vascular procedure.

Host responses to the implanted foreign body material may include, for example, infection and inflammation. Accordingly a variety of therapeutic agent (s) may be added (singly or in combination) to the collagen matrix. Examples of therapeutic agents that could be added include anti-proliferative agents, like rapamycin, tacrolimus and paclitaxel, anti-inflammatory (e.g., NSAIDS) hormones (e.g., estrogen) and antibiotics.

In particular, the method comprises the steps of: combining the therapeutic agent(s) with the matrix (e.g., collagen matrix) and placing the therapeutic agent imbibed sleeve perivascularly so as to cover the site of vascular access with anticipation of the local release of the drug(s).

In addition to having application in sealing puncture sites associated with cardiac and vascular catheterization procedures, the present invention is deemed useful and applicable to various diagnostic and therapeutic interventional procedures including atherectomies, stent implantation, rotablators, thrombolysis therapy, laser angioplasty, valvuloplasty, aortic prosthesis implantation, intraortic balloon pumps, pacemaker implantation and electrophysiology studies as well as in patients with congenital heart disease and those undergoing dialysis and procedures relating to percutaneous extracorporeal circulation. The present invention may be used in both adults and children independent of the age of the vessel to be sealed.

The inventive method may be practiced with any embodiment of a device suitable for delivery of therapeutic agents to regulate the tissue response to vascular procedures or devices. In one embodiment, the device is a sheet of matrix material such as collagen cylindrically shaped to fit over a vessel at the site of puncture or incision like a sleeve, to deliver therapeutic agents extravascularly. The sleeve may be secured to the vessel by sutures, self-adhesion, or stabilized over the vessel by suturing the free edges of the sleeve to one another thereby providing a snug fit over the vessel wall.

In another embodiment, the device may be constructed to deliver a plug of hemostatic material imbibed with a therapeutic agent, to seal a puncture or incision or other breach of the vessel wall. In yet another embodiment, the device may be used to envelop a puncture site, incision or other breach of the vessel wall from the interior, interior and exterior and/or exterior of the vessel. The device comprises a tissue response regulating amount of a therapeutic agent and a biological sealant or hemostatic device.

BRIEF DESCRIPTION OF FIGURES

FIGS. 1A, 1B, 2A, and 2B illustrate preferred embodiments of the present invention;

FIGS. 2A and 2B illustrate another embodiment of the present invention in which an exterior support or skeletal structure is employed;

FIGS. 3A-3C illustrate a self-interlocking embodiment of this invention;

FIG. 4A illustrates another example of a self-interlocking design of the present invention where a representative shunt opening 20 including two shunt contact wings or flaps 21 are also shown;

FIG. 4B illustrates another example of a self-interlocking design of the present invention where lock 18 may be inserted into window 19 from the inside toward the outside;

FIGS. 6-13 illustrate various possible deployments of the drug-eluting sleeve of the present invention in view of various vessel reparative needs;

FIGS. 18A, 18B, 19A, 19B, and 20 illustrate some results obtained using the present invention;

DETAILED DESCRIPTION

Figure 5:
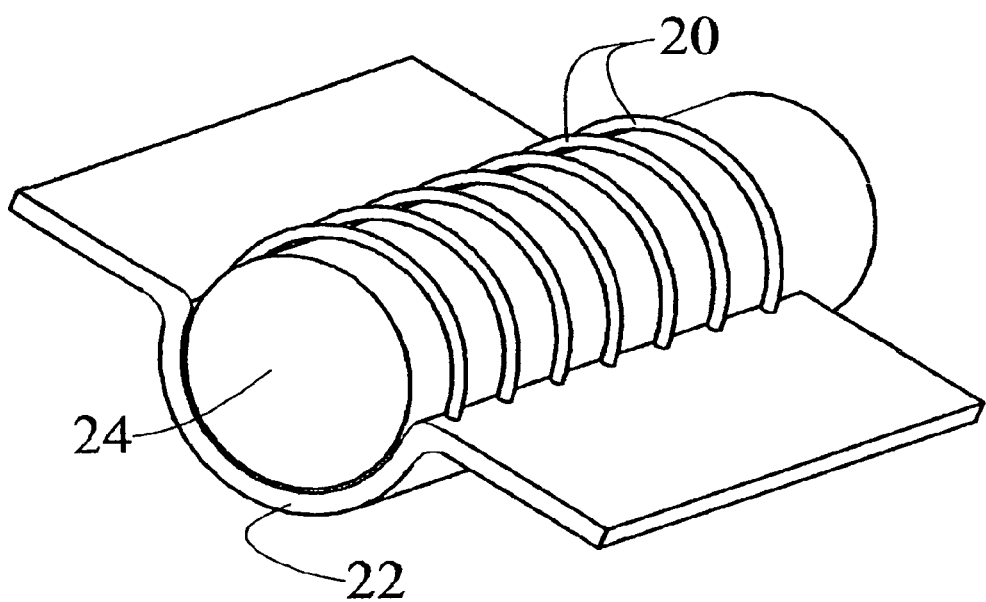
FIG. 5 shows the basic device shown in FIGS. 1A, 1B, 2A, and 2B including an exterior wire support or framework, which assists retention of sleeve shape.
Figure 6:
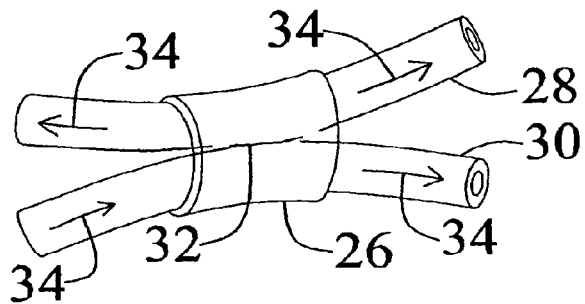
Figure 7:
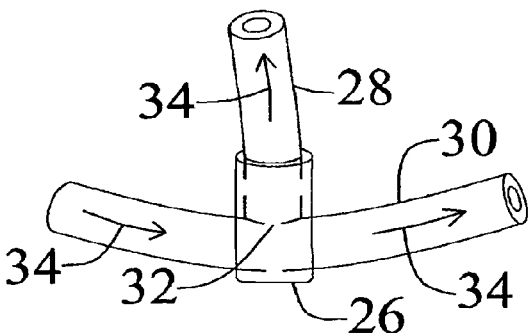
Figure 8:
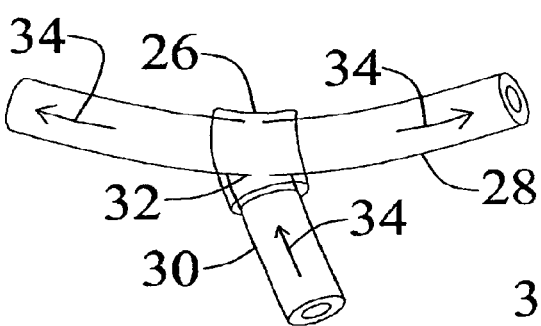
Figure 9:
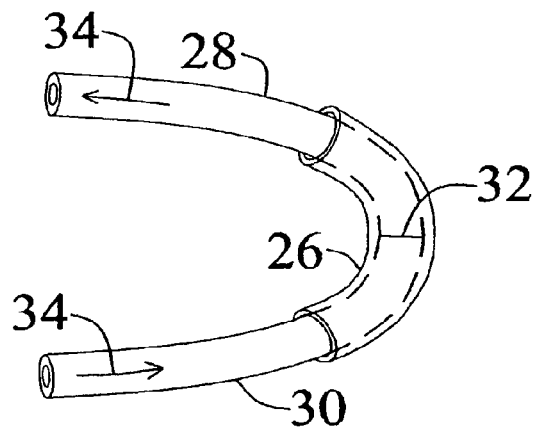
Figure 10:
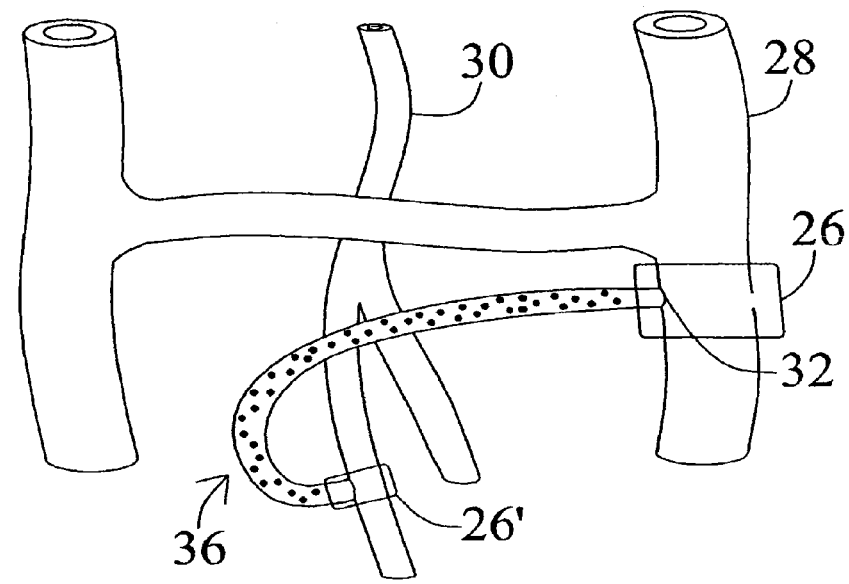
Figure 11:
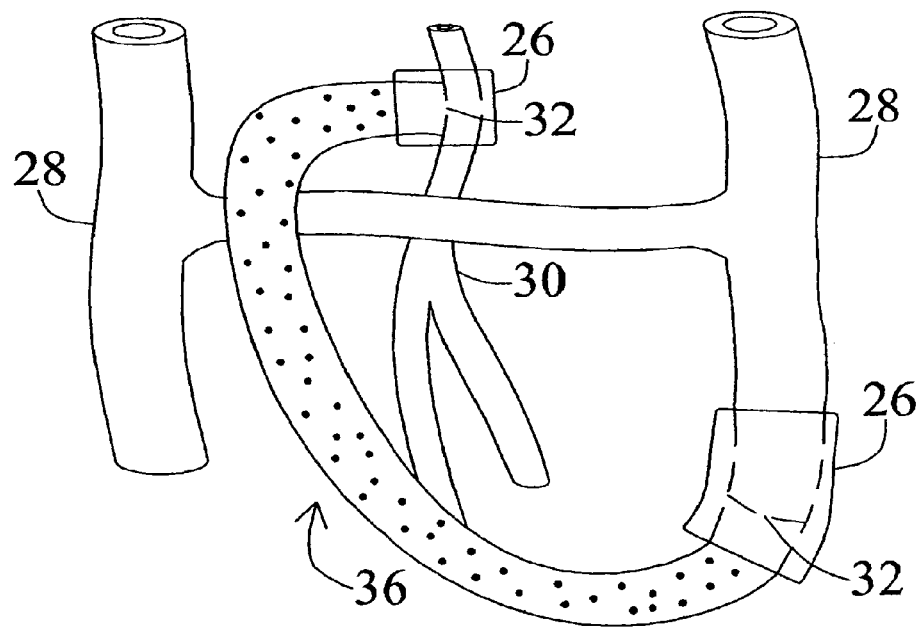

The medical devices of the present invention broadly comprise one or more therapeutic agents imbibed in one or more biocompatible matrices. In one aspect, the present invention is a sleeve comprising a therapeutic agent eluting matrix material combined with a therapeutic agent that can be delivered extravascularly to prevent, suppress, or treat vasculoproliferation.

In another aspect, the present invention is a matrix material combined with a therapeutic agent, the composition in the form of a plug, wherein the plug can be used to seal a vascular puncture site and to deliver a tissue response regulating amount of a therapeutic agent. In yet another aspect, the present invention provides an anchoring device for the therapeutic agent imbibed matrix. In a further aspect, the present invention forms a "sandwich" configuration around a vascular puncture, to close the puncture intravascularly as well as extravascularly and to deliver therapeutic agents.

A. Therapeutic Agents

The therapeutic agents that may be added to the matrix material include a substance selected from a group consisting of anti-inflammatory drugs, smooth muscle cell growth inhibitors, endothelial cell stimulators, antineoplastic reagents, antibiotics, blood clotting inhibitors, genetic material, and mixtures thereof. As used herein, "anti-inflammatory drug" refers to a substance that reduces inflammation by acting on body mechanisms. "Stimulator of endothelial cell growth" refers to a substance that stimulates the growth and/or attachment and/or chemotaxis of endothelial cells. "Antineoplastic reagent" refers to any substance preventing or arresting the development, maturation, or spread of neoplastic cells. "Antibiotic" refers to a soluble substance derived either naturally from a mold or bacteria or synthetically that inhibits the growth of microorganisms.

The term "therapeutic agent" means any agent possessing pharmacological activity in preventing, suppressing, or treating the smooth muscle cell proliferation involved in neointimal hyperplasia, stenosis, restenosis, or failure of vascular grafts or procedures, or any agent that regulates tissue response. The agent may, if desired, be in the form of a free base, a free acid, a salt, an ester, a hydrate, an amide, an enantiomer, an isomer, a tautomer, a prodrug, a polymorph, a derivative, an analogue, or the like, provided that the free base, free acid, salt, ester, hydrate, amide, enantiomer, isomer, tautomer, prodrug, polymorph, derivative, or analogue is suitable pharmacologically, i.e., effective in the present methods, compositions, and devices.

1. Antiproliferative Agents

Examples of therapeutic agents with actions that include inhibition of smooth muscle cell or fibroblast growth (one aspect of an antiproliferative effect) include, but are not limited to, acetylsalicylic acid (aspirin), actinomycin D, angiopeptin, angiostatin, azathioprine, brequinar sodium, cisplatin, cyclosporin A, desferoxamine, deoxyspergualin, endostatin, enoxaprin, estrogen, flavoperidol, fluorouracil, halofuginone, hirudin, matrix metalloproteinase inhibitors, mizaribine, mitoguazone, mycophenolic acid morpholino ester, paclitaxel, taxanes, epothilones, raloxifene, rapamycin (sirolimus), analogues of rapamycin, everolimus, ABT 578, Biolimus, tacrolimus (FK506), vinblastine, vincristine, vitamin K, nitric oxide donors such as nitrosoglutathione, substrates for nitric oxide production such as L-arginine, and derivatives and mixtures thereof.

Derivatives of these compounds may also be used, e.g., 40-O-(2-hydroxy)ethylrapamycin or everolimus, a structural derivative of rapamycin (sirolimus), also known as SDZ-RAD (Serkova et al., Br. J. Pharmacol. (2001) 133: 875-885; Hausen et al., Transplantation (2000) 69: 76-86); other analogues of rapamycin (sirolimus) such as ABT-578, CCI-779, 7-epitrimethoxyphenyl rapamycin, 7-thiomethyl rapamycin, 7-epirapamycin, 7-epi-thiomethyl rapamycin, 7-demethoxy rapamycin, 30-demethoxy rapamycin, 27-desmethyl rapamycin, and 26-dihydro rapamycin, 33-deoxo-33-(R)-hydroxyrapamycin; and the estrogen derivative 17β-estradiol.

Therapeutic agents with antiproliferative effects useful in the methods, compositions, and devices of the present invention include substituted macrocyclic compounds with antiproliferative activity, including a substituted compound of Formula I:

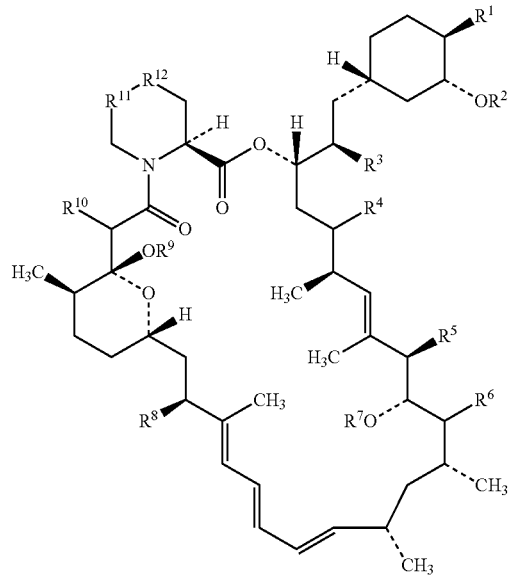

(Formula I)

wherein $R^1$ is hydrogen, alkoxyhydroxyl, alkylalkoxycarbamoyl, tetrazolyl, or —$OR^{14}$ wherein $R^{14}$ is hydrogen, alkyl, alkenyl, alkynyl, aryl, arylalkyl, thioalkyl, hydroxyalkyl, hydroxyaryl, hydroxyarylalkyl, hydroxyalkoxyalkyl, hydroxyalkylarylalkyl, dihyroxyalkyl, dihyroxyalkylarylalkyl, alkoxyalkyl, acyloxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihyroxyalkylallyl, dioxolanylallyl, carbalkoxyalkyl, or alkylsilyl, hydroxyl, carboxyl, cyano, halogen, epoxy, sulfohalo, sulfoalkyl, sulfoaryl, sulfoarylalkyl, sulfoheterocyclic, sulfoheterocyclicalkyl, sulfoamidoalkyl, sulfoamidoaryl, oxoalkyl, oxoaryl, oxocycloalkyl, oxoarylalkyl, oxoheterocyclic, oxoheterocyclicalkyl, carboxyl, carboxycycloalkyl, carboxyaryl, carboxyheterocyclic, carboxy(N-succinimidyl), alkylalkoxycarbonyl, carbamoylalkyl, alkylcarbamoylalkyl, carbamoylalkenyl, carbamoylalkynyl, alkoxycarbamoyl, carbamoylcycloalkyl, —$N_3$, or —$R^{18}$—$R^{15}$—$R^{16}$—$R^{17}$ wherein $R^{18}$ is oxo, alkyl, or amidoalkyl, $R^{15}$ is nitrogen, and $R^{16}$ and $R^{17}$ are independently selected from hydrogen, alkyl, alkenyl, alkynyl, alkoxy, cycloalkyl, cycloalkenyl, cycloalkynyl, hydroxyl, carboxyl, cyano, aryl, heterocyclic, and arylalkyl;

$R^2$ is hydrogen, halogen, hydroxyl, alkyl, alkenyl, alkynyl, aryl, acyl, acyloxy, aryloxy, alkylthio, alkylsulfinyl, oxo, or together with $R^{14}$ forms $C_{2-6}$ alkylene;

$R^3$, $R^5$, $R^7$, $R^9$, and $R^{19}$ are independently selected from hydrogen, halogen, hydroxyl, alkyl, alkenyl, alkynyl, aryl, acyl, acyloxy, aryloxy, alkylthio, alkylsulfinyl, and oxo;

$R^4$ is hydrogen, hydroxyl, oxo, diazo, phenyl-substituted alkyl, =$CH_2$, —O—$(CH_2)_2$—O—, —S—$(CH_2)_2$—S—, —O—$(CH_2)_3$—O—, —S—$(CH_2)_3$—S—, or =N—$N(R^{19})(R^{20})$ wherein $R^{19}$ and $R^{20}$ are independently selected from hydrogen, alkyl aryl, arylalkyl, heterocyclic, and heterocyclicalkyl;

$R^6$ is hydrogen, hydroxyl, oxo, phenyl-substituted alkyl, —$OR^{21}$ wherein $R^{21}$ is $C_{1-4}$ alkyl, alkylcarbonyl, arylcarbonyl, heteroarylcarbonyl, hydroxyalkylcarbonyl, aminoalkylcarbonyl, formyl, or aryl;

$R^8$ is alkoxy, oxo, —$OR^{13}$, —$S(O)_xR^{13}$, or —$NR^{13}$ wherein $R^{13}$ is hydrogen, aryl, alkyl, alkenyl, alkynyl, hydroxyalkyl, hydroxyalkenyl, hydroxyalkynyl, benzyl, alkoxybenzyl, or chlorobenzyl and x is 0, 1, or 2; and $R^{11}$ and $R^{12}$ are —$CH_2$—, —S—, or >S=O.

2. Antibiotic Agents

Antibiotics are used to prevent infection after implantation of the matrix. Preferred antibiotics include, but are not limited, to all broad and medium spectrum agents, including penicillins, aminoglycolides, cephalosporins (1st, 2nd, and 3rd generation), macrolides (rapamycin, for example, is a macrolide antibiotic), tetracyclines, and derivatives and mixtures thereof. Such therapeutic agents and all analogues, derivatives, isomers, polymorphs, enantiomers, salts, and prodrugs thereof may be used in the present invention.

3. Anti-Inflammatory Agents

Examples of therapeutic agents with anti-inflammatory effects include, but are not limited to, acetylsalicylic acid (aspirin), angiopoietin-1, atorvastatin, rapamycin, analogues of rapamycin, steroids (e.g., dexamethasone), non-steroidal anti-inflammatory agents like indomethacin, $COX_{-2}$ inhibitors (see Merck Index (13th Ed.). Such therapeutic agents and all analogues, derivatives, isomers, polymorphs, enantiomers, salts, and prodrugs thereof may be used in the present invention.

4. Other Therapeutic Agents

Other therapeutic agents may be selected from the group consisting of anticoagulants (e.g., heparin, hirudin, vitamin K), direct thrombin inhibitors, antilipemic agents (e.g., atorvastatin, cerivastatin, simvastatin, lovastatin), antimetabolites, antineoplastic agents (e.g., cisplatin, methotrexate), antiplatelet agents (e.g., clopidogrel, ticlopidine, diflunisal), antithrombins, antirheumatics, calcium channel blockers, cells (e.g., bone barrow, stem, vascular), corticosteroids, IIbIIIa antagonists, immunomodulators, immunosuppressants (mycophenolate mofetil), and recombinant DNA or proteins (list based in part on the Merck Index (13th Ed.)). Specific compounds within each of these classes may also be selected from any of those listed under the appropriate group headings in *Comprehensive Medicinal Chemistry*, Pergamon Press, Oxford, England (1990), pp. 970-986, the disclosure of which is incorporated herein by reference.

Yet another additive is a stimulator of endothelial cell growth. Preferred stimulators of endothelial cell growth include basic fibroblast cell growth factor, endothelial cell growth factor, alpha$_2$ macroglobulin, vitronectin, fibronectin, fibronectin fragments containing binding determinants for endothelial cells, and derivatives and mixtures thereof. The stimulator is generally used at pharmacological concentrations. Specifically, fibronectin preferably has a concentration ranging from about 5 to about 150 ng/ml.

Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric, and galacturonic acids.

The present invention also includes prodrugs of the therapeutic agents and their salts. The term "prodrug" refers to a drug or compound in which the pharmacological action or active curative agent results from conversion by metabolic processes within the body. Prodrugs are generally considered drug precursors that, following administration to a subject and subsequent absorption, are converted to an active or a more active species via some process, such as a metabolic process. Other products from the conversion process are easily disposed of by the body.

Prodrugs generally possess a chemical group that renders them less active or confers solubility or some other property to the drugs. Cleaving of the chemical group generates the more active drug. Prodrugs may be designed as reversible drug derivatives and utilized as modifiers to enhance drug transport to site-specific tissues. The design of prodrugs to date has been to increase the effective water solubility of the therapeutic compound for targeting to regions where water is the principal solvent (Fedorak, et al., *Am. J. Physiol.* (1995), 269: G210-218, describing dexamethasone-beta-D-glucuronide; McLoed, et al., *Gastroenterol.* (1994), 106: 405-413, describing dexamethasone-succinate-dextrans; Hochhaus, et al., *Biomed. Chrom.* (1992), 6: 283-286, describing dexamethasone-21-sulphobenzoate sodium and dexamethasone-21-isonicotinate).

Prodrugs are also discussed in Sinkula et al., *J. Pharm. Sci.* (1975), 64:181-210, in Higuchi, T. and Stella, V., *Pro-Drugs as Novel Delivery Systems*, Vol. 14 of the A.C.S. Symposium Series, and in *Bioreversible Carriers in Drug Design* (Ed. Edward B. Roche), American Pharmaceutical Association and Pergamon Press (1987).

The present invention also includes derivatives of the therapeutic agents. The term "derivative" refers to a compound that is produced from another compound of similar structure by the replacement or substitution of one atom, molecule, or group by another. Salts, esters, hydrates, amides, enantiomers, isomers, tautomers, prodrugs, polymorphs, derivatives, and analogues of the pharmaceutical agents may be prepared using standard procedures known to those skilled in the art of synthetic organic chemistry and described, for example, in March, J., *Advanced Organic Chemistry: Reactions, Mechanisms and Structure* (4$^{th}$ Ed.), Wiley-Interscience, New York (1992).

The present invention can typically contain an amount of therapeutic agent from about 0.001 μg to about 200 μg per mg weight of the composition. The dose of the therapeutic composition that is administered and the dosage regimen for treating the condition or disease depend on a variety of factors, including the age, weight, sex, and medical condition of the subject, the severity of the condition or disease, the route and frequency of administration, the time of administration, the rate of excretion, any synergistic or potentiating activity of any combined agents, and the specific activity of the agent, and can therefore vary widely, as is well known.

Table 1 below lists some of the various therapeutic agents contemplated in this invention.

TABLE 1

Therapeutic Agents

| Common or Chemical Name | Alternative Names and References |
|---|---|
| Rapamycin ((3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2[(1S,3R,4R)-4-hydroxy-3-methoxycyclohexyl]-1-methylethyl]10,21-dimethoxy-6,8,12,14,20,26-hexamethyl-23,27-epoxy-3H-pyrido[2,1-c][1,4] oxaazacyclohentriacontine-1,5,11,28,29 (4H,6H,31H)-pentone) | Sirolimus; Rapamune ®; *Merck Index* (13th Ed.), at monograph 8202, p. 1454 |
| Rapamycin 42-ester with 3-hydroxy-2-(hydroxymethyl)-2-methylpropionic acid | CCI-779; WO 02/40000; U.S. Pat. Pub. No. 20030050222 |
| 42-Epi-(tetrazolyl)-rapamycin | ABT-578; U.S. Pat. No. 6,015,815; U.S. Pat. Pub. No. 20030129215; U.S. Pat. Pub. No. 20030123505 |
| 4-Dimethylamino-but-2-enoic acid [4-(3-chloro-4-fluoro-phenylamino)-3-cyano-7-ethoxy-quinolin-6-yl]-amide | EKB-569; U.S. Pat. Pub. No. 20030050222 |
| 40-O-(2-hydroxyethyl)-rapamycin | Everolimus; SDZ-RAD; RAD001; Certican; U.S. Pat. Pub. No. 20010041179; *Eur. J. Cardiothorac. Surg.* 2003, 24: 154-158; *Expert Opin. Investig. Drugs* 2002, 11: 1845-57; *N. Engl. J. Med.* 2003, 349: 847-858 |
| 16-O-substituted rapamycins | WO 94/02136; WO 96/41807 |
| 40-O-substituted rapamycins | WO 94/09010; WO 92/05179; WO 95/14023; WO 94/02136; WO 94/02385; WO 96/13273 |
| 20-Thiarapamycin | *Org. Lett.* 2003, 5: 2385-2388 |
| 15-Deoxo-19-sulfoxylrapamycin | *Org. Lett.* 2003, 5: 2385-2388 |
| 32-Deoxorapamycin | SAR 943; *Immunology* 2003, 109: 461-467; *Am. J. Respir. Crit. Care Med.* 2003, 167: 193-198 |
| 33-Deoxy-33-hydroxyrapamycin | U.S. Pat. No. 5,138,051; U.S. Pat. No. 5,169,851; U.S. Pat. No. 5,202,332 |
| Paclitaxel | *Merck Index* (13th Ed.), at monograph 7052, p. 1251 |
| N-debenzoyl-N-(2-thenoyl) butitaxel | *J. Med. Chem.* 1997, 40: 236-241 |
| N-debenzoyl-N-tert-butoxycarbonyl-10-deacetyl taxol | Taxotere; Docetaxel; RP 56976; NSC 628503; *Cancer Res.* 1991, 51: 4845-4852; *J. Natl. Cancer Inst.* 1991, 83: 288-291 |
| Pimecrolimus | U.S. Pat. Pub. No. 20030170287; *Eur. J. Dermatol.* 2002, 12: 618-622 |
| LF 15-0195 (analogue of 15-deoxyspergualin) | *Transplantation* 2003, 76: 644-650 |
| Sanglifehrin A | *J. Immunol.* 2003, 171: 542-546 |
| Mycophenolate mofetil | U.S. Pat. Pub. No. 20030181975; *Transplantation* 2003, 75: 54-59 |
| Actinomycin D | U.S. Pat. Pub. No. 20030181482; U.S. Pat. Pub. No. 20030181975 |
| Acetylsalicylic acid | Aspirin; *Merck Index* (13th Ed.), at monograph 856, p. 145 |
| Dexamethasone | *Merck Index* (13th Ed.), at monograph 2960, p. 518 |

5. Synergism and Potentiation of Therapeutic Agents

In an embodiment of the present invention, two or more therapeutic agents are combined with the matrix material to enhance the pharmacological effect of the methods and devices of the invention, synergistically or potentiationally to increase the effect of one or more of the therapeutic agents. The therapeutic agents may have similar or different pharmacological activities, be combined in one matrix, be imbibed in separate matrix layers, or be otherwise combined with the matrix as synergistically or potentiationally advantageous for practicing the invention.

Isobolograms may be used to study the combined effects of two pharmacological agents. Here, the concentration of each drug alone that produces a certain endpoint (e.g., 50% inhibition of cell growth) is plotted on the two graphical axes. The straight line connecting the two points represents equally effective concentrations of all combinations of the two drugs if the interaction is purely additive. A shift of the isobologram to the left of the predicted cytotoxicity (curve with concave side up) represents a synergistic interaction.

Conversely, a shift to the right (curve with convex side up) represents an antagonistic interaction. When isobolograms for different endpoints are plotted on the same graph, the concentration of each drug is expressed as the fraction of the concentration of each drug alone that produced the same effect. This produces a symmetrical isobologram with unitless measures on each axis and allows a direct comparison of different endpoints.

B. Biocompatible Matrix or Sealant

In the present invention, the matrix or sealant material (or a "hemostatic device") creates a delivery depot or reservoir for the therapeutic agent and controls the delivery kinetics. Material for the matrix may be from natural sources or synthetically manufactured, or a combination of the two. A device of this invention may employ a biocompatible, biodegradable resorbable matrix material such as chitosan, collagen, or fibrin. A suitably biocompatible, nonbiodegradable matrix may also be used. Thus, a combination of biodegradable and nonbiodegradable substances, two or more biodegradable substances, or two or more nonbiodegradable substances may be selected for the matrix material.

Important in the selection of a particular matrix material is the porosity of the material and, where applicable, durability or a controllable rate of biodegradation, as well as the ability to interact with clotting factors in the blood and tissue to initiate hemostasis. The porosity of the matrix influences the drug binding and elution capacity. The durability of the matrix reflects the time required for complete reabsorption of the matrix material and also influences the drug delivery capacity, since as the matrix material degrades, it elutes the drug. Both porosity and durability can be controlled and varied as advantageous for practicing the invention. The characteristics with respect to porosity, rate of biodegradation, thickness, etc., need not be identical throughout the matrix.

Collagen (Type I) is a preferred material for the matrix or sealant of the drug eluting device of the present invention. Collagen is biocompatible, biodegradable, resorbable, naturally occurring, and non-toxic. Collagen exhibits a high degree of flexibility and mechanical durability, as well as intrinsic water wettability, semipermeability, and consistent flow characteristics. In addition, collagen has favorable degradation or resorption characteristics, and, as is well known in the art, the rate at which resorption of the collagen occurs can be modified by cross-linking the protein.

The collagen may be from an animal or a human source or produced using recombinant DNA techniques. Any type of collagen, e.g., Types II, III, V, or XI, alone or in combination with Type I, may be used. Although collagen matrix in the form of a sheet, or membrane, or plug is the preferred embodiment of this invention, other forms of collagen, e.g., gel, fibrillar, sponge, tubular, etc., may also be used. A collagen matrix in the form of a sheet or membrane may be about 0.1-5 mm thick and produced in a wide range of effective pore sizes, from about 0.001-100 μm or even larger. This internal pore network creates a high surface area and serves as a microreservoir for storage and delivery of a therapeutic agent.

Another protein matrix or sealant suitable for drug delivery is made of fibrin. A fibrin matrix is comprised of cross-linked fibrin units that are a reticular network of thrombin-modified fibrinogen molecules. This matrix is similar to a natural blood clot. In contrast to a natural blood clot, however, the size of pores in a fibrin matrix can be controlled and varies from about 0.001-0.004 mμ (millimicrons, so-called micropores). The differences in pore sizes between collagen and fibrin matrices permit the binding of therapeutic agents for distinct rates of drug release. The ability to control bleeding, remain firmly fixed in place, and naturally degrade makes fibrin a good matrix material for drug delivery and confers some advantages over synthetic matrices. Early applications of fibrin as a matrix have been for delivery of antibiotics and other biologics.

Fibrin matrices are prepared in a dry granular form (International Application No. PCT/EP99/08128). This formulation, manufactured by HyQSolvelopment (Binzen, Germany; HyQ-Granuseal) using fluid bed granulation, contains D-mannitol, D-sorbit, fibrinogen-aqueous solution, and a thrombin-organic suspension. Dry fibrin may be used in wound closure, promotion of healing, and homeostasis. However, application of such a formulation in drug delivery is limited because it does not allow for a target-oriented shaping of solid particles around the vessel wall and delivery of exact doses. Dry fibrin particles have low porosity and poor physical stability.

Another potentially useful matrix or sealant material is chitosan. Chitosan is a natural polymer and biodegradable. It has proven to be a useful biocompatible aminopolysaccharide and a matrix for controlled release of therapeutic agents for local delivery. Chitosan implants cause no systemic and local side effects or immunologic responses. Chitosan can be prepared from the degradation of slow chitin (mol wt $1 \times 10^6$) using high temperature sodium hydroxide hydrolysis, to a molecular weight of $5 \times 10^5$. However, the inability to control porosity is a disadvantage of chitosan as matrix material.

C. Optional Adjuvants

A device of this invention optionally includes agents (hereafter adjuvants) that accomplish other objectives, e.g., that inhibit collagen accumulation and help reduce calcification of the vascular wall. Early research has shown a relationship between local vessel trauma and expedited calcification. Recently, a study in humans has shown that the matrix Gla-protein (protein γ-carboxylated vitamin K-dependent γ-carboxylase) is constitutively expressed by normal vascular smooth muscle cells and bone cells. High levels of Gla-protein mRNA and non-γ-carboxylated protein were found in atherosclerotic vessel tissues.

This γ-carboxylated protein is necessary to prevent or postpone the onset of vascular calcification (Price et al., Arterioscler. Thromb. Vasc. Biol. (1998) 18: 1400-1407). These data indicate that calcification caused by injury must be actively inhibited. Introduction of pharmaceuticals that prevent calcium accumulation helps to postpone calcification and the restenotic processes.

In this invention, local delivery of vitamin K counteracts the calcification effect associated with vessel injury, by timely activation of γ-carboxylase (in this case Gla-protein), and ensures that other calcium-binding proteins function properly and do not bind excess calcium (Hermann et al., Arterioscler. Thromb. Vasc. Biol. (2000) 20: 2836-2893). A mixture of vitamin K along with other antiproliferative drugs may be used.

The acute response to any injury, including surgical trauma, characterized by an inflammatory reaction is an attempt to limit disturbances in homeostasis. Hallmarks of this inflammatory reaction include leukocyte accumulation, increased fibrin deposition, and release of cytokines. Addition of synthetic glucocorticoids like dexamethasone decreases this inflammatory response and may eventually decrease the restenotic process. Since the pharmacological mechanisms of action of antiproliferative agents and synthetic glucocorticoids are different, agents with different "antirestenotic mechanisms" may be expected to act synergistically. Thus, it may be useful to combine two or more of these agents. In light of the present disclosure, numerous other anti-proliferative or anti-stenosis drugs and other suitable therapeutics and adjuvants will likely occur to one skilled in the art.

D. Example Compositions Useful for Practicing the Invention

Each of the above therapeutic agents can be mixed with the matrix material either alone or in combination. Depending on the therapeutic agent, the agent can be combined with the matrix using physical, chemical, or biological methods. A combination of techniques can be used. One skilled in the art will appreciate that the concentration of the therapeutic agent need not be and often will not be uniform throughout the entire matrix, and the device can comprise one or more layers, which release the therapeutic agents at different rates. In a multilayered device for example, the topmost layer, the surface that will abut the vascular wall can be composed of plain matrix without any drug. The layer immediately below can have "drug A" with anti-proliferative and/or anti-inflammatory and/or antibiotic properties. The next matrix layer can either have no drug, the drug same, a similar drug or a different drug than drug A and so on. The matrix material in each of these layers may be same or different. Even within the same matrix, by altering properties like the pore size, the drug delivery kinetics can be varied. The concentration of the drug need not be uniform throughout the matrix All of the foregoing therapeutic agents, biocompatible matrix (or sealant) materials, and optional adjuvants may comprise any number of the therapeutic agents stated herein or advantageous for the condition or disease to be treated. Matrix material can be defined by weight or physical dimension (e.g., 3×2 cm rectangle or circle having a diameter of about 1 cm square or it can be specified using weight e.g., in milligrams of the matrix). The dose of therapeutic agents may be defined in different ways for example by absolute weight in pico, nano, micro, milli or gram quantities, where appropriate in units or international units, in relation to the weight of the matrix e.g., microgram per milligram of the matrix, in relation to the physical dimension of the matrix e.g., micrograms per square mm or square cm of the matrix.

In addition, drug formulations and carrier materials useful in the present invention are discussed in Remington: The Science and Practice of Pharmacy (19th Ed.), Mack Publishing Co., Pennsylvania (1995), in Hoover, J. E., Remington's Pharmaceutical Sciences, Mack Publishing Co., Pennsylvania (1975), in Pharmaceutical Dosage Forms (Liberman, H. A. and Lachman, L., Eds.), Marcel Decker, New York (1980), and in Pharmaceutical Dosage Forms and Drug Delivery Systems (7th Ed.), Lippincott, Williams & Wilkins (1999).

The composition of the present invention may be in the form of a package containing one or more of the compositions. The composition may be packaged per application, use, device, or procedure. The package may also contain a set of instructions. The composition may be useful for the treatment of mammals, reptiles, rodents, birds, farm animals, and the like, including humans, monkeys, lemurs, horses, pigs, dogs, cats, rats, mice, squirrels, rabbits, and guinea pigs.

E. Drug Elution

The process of elution of therapeutic agent from the matrix or sealant material to and/or through the vessel wall is merely illustrative of one possible drug delivery process. The terms, "effective amount" and "tissue response regulating amount" mean the amount of the therapeutic or pharmacological agent effective to elicit a therapeutic or pharmacological effect, including, but not limited to, preventing, suppressing, or treating vasculoproliferation, infection, inflammation, neointimal hyperplasia, stenosis, restenosis, or fibrous tissue formation without undue adverse side effects, either in vitro or in vivo. The therapeutic agent should be administered and dosed in accordance with good medical practices, taking into account the clinical condition of the individual patient, the site and method of administration, scheduling of administration, and other factors known to medical practitioners. In human therapy, it is important to provide a dosage form that delivers the required therapeutic amount of the drug in vivo and renders the drug bioavailable in a rapid or extended manner. The therapeutic amount can be experimentally determined based on, for example, the rate of elution of the agent from the matrix, the absorption rate of the agent into the blood serum, the bioavailability of the agent, and the amount of serum protein binding of the agent.

F. Devices Useful for Practicing the Invention

In a conventional percutaneous procedure, vascular access is obtained by inserting a needle percutaneously through the skin into a blood vessel (e.g. artery or vein). The flexible end of a guidewire is passed through the needle into the blood vessel. The needle is then removed to leave only the guidewire in place. A conventional introducer sheath and an arterial dilator are then passed over the guidewire and into the artery. The guidewire and dilator are removed, and the sheath is left in place.

A catheter or other intravascular instrument is then inserted through the sheath and advanced in the lumen of the blood vessel to the target location, such as the site of atherosclerosis. An intravascular procedure such as angiography or angioplasty is performed. With the procedure completed, the catheter and then the sheath are removed. Once the sheath is removes hemostasis needs to be achieved. The most common technique is to apply manual digital pressure to the percutaneous puncture site until hemostasis occurs.

Instead, following a diagnostic or interventional catheterization procedure, the present invention may be applied directly to the site of vascular access or puncture, eliminating the need for mechanical pressure. In a preferred embodiment, the biological sealant matrix will seal the vascular access or puncture and also release one or more therapeutic agents from the matrix into the vessel wall and surrounding tissue to prevent or reduce any tissue responses to the matrix material. Because the matrix is biodegradable and applied externally to the vasculature, together with one or more therapeutic agents, the invention will minimize, eliminate or treat any inflammation, infection or other undesirable, tissue reaction to the implanted matrix. This therapeutic composition not only achieves hemostasis, but also reduces or eliminates tissue response (e.g., inflammation or infection) related to the implanted matrix. This helps the healing process, and helps maintain the option of future vascular access from the same site, and helps eliminate or reduce patient discomfort or pain when healing from invasive vascular procedures.

The present invention may be practiced in various device forms, including, but not limited to, the sleeve, plug, sponge, anchor, or sandwich forms. The device of the present invention may comprise a single, double, or multiple layers. In a preferred embodiment of the invention as a single layer sleeve form, the protein matrix is a sheet or membrane of Type I bovine collagen, and the therapeutic agent is rapamycin (sirolimus). A relatively flat sheet of collagen is either impregnated, absorbed, adsorbed, saturated, dispersed, or immobilized with rapamycin (sirolimus). About 0.2 µg/cm$^2$-2 mg/cm$^2$, preferably 120 µg/cm$^2$, of rapamycin (sirolimus) is combined with the collagen matrix material, which in the dry form is a sheet that is 0.3-3.0 mm thick.

The rapamycin imbibed collagen sheet or sleeve may be modified into a tube or other geometrical shapes and directly secured to the outside of the native vessel, at the site of graft anastamosis or over the vein, artery, or graft itself. The sleeve may be secured at the desired site by sutures or staples. The suture material itself may be combined with a therapeutic agent. In this aspect, the therapeutic agent permeates through the vessel wall and into the lumen. The rate of drug elution from the membrane can be varied, and elution can continue until the matrix material is completely resorbed.

In another aspect, the present invention may be a double or multiple layer sleeve comprising an antiproliferative-imbibed, inner matrix layer and an external support skeletal structure or layer. In this embodiment, the inner matrix material is a sheet or membrane of Type I collagen about 0.3-3 mm thick, and the exterior skeletal support material structure is a sheet of PTFE about 0.3-3 mm thick. The antiproliferative drug, in this embodiment, is rapamycin in an amount of about 0.2 µg to 100 mgs/mg of matrix. The sheet of collagen may be attached to the PTFE sheet using a variety of techniques, e.g., physically using sutures, adhesives, staples, or chemically by bonding.

The two sheet composite can be rolled to create either a tubular structure or geometrical variations thereof. The composite device or sleeve is then suitably trimmed so that it can be applied over the desired site—artery, vein, graft anastomotic site, etc. The free edges of the PTFE sleeve are attached to each other by adhesive, sutures, staples, etc. This stabilizes the entire device on the outside of the vascular structure or graft. The drug then permeates through the vascular or prosthetic material wall, and while in the wall, the drug inhibits smooth muscle cell proliferation, an integral part of the healing response that follows surgical construction of the graft.

After a period of time (the period can be varied based on degree of cross linking—from a few days to several months) the body breaks down and absorbs the collagen, leaving its exterior support skeleton or structure intact. One skilled in the art will appreciate that the body-resorbable aspect of the protein layer chosen to imbibe the drug is an optional preferred practice of the present invention. The PTFE, not being bioabsorbable, tends to hold the resorbable protein layer in place for a length of time sufficient for the drug to permeate through the vascular structure, graft, or prosthetic material wall. The external PTFE layer serves to keep the drug in close apposition with the outer aspect of the vessel or graft wall and limits its diffusion to the surrounding tissues and skin.

The external layer may have advantages in addition to those from supporting the drug eluting inner membrane or matrix material. For example, the external PTFE skeleton can function as an additional reinforcement layer and prophylactically address problems related to a weak scar, graft disruption, or aneurysm formation. Although the desired effect of the imbibed drug is the ability to inhibit the smooth muscle cell proliferative response, it is this proliferative response that contributes to the formation of a surgical scar of good quality or adequate firmness. A weak scar at the site of surgical anastomosis can potentially lead to graft disruption or aneurysm formation.

Also contemplated as within the present invention is an exterior skeletal or support layer that is itself biodegradable. Thus, a resorbable external skeletal structure combined with a resorbable internal drug eluting collagen layer—the two layers having the same or different rates of degradability and resorption—would generate a healed vascular or graft structure without any foreign material remaining after the procedure. One skilled in the art would understand in view of this disclosure that numerous other such materials are likely to be usable in this invention. For example, Dacron® polyester can be a suitable material for the external support structure.

The present invention also provides for device self-fixation to the outer surface of the vascular wall. The device could be made more adhesive to the vascular wall if, in the final stage, collagen is combined with fibrin sealant, acetylated collagen, or photoreactive groups such as fluorescein isothiocyanate or Rose Bengal, both from Sigma-Aldrich Corp. (St. Louis, Mo.). Fibrin sealant and acetylated collagen have been found to increase adhesion of collagen matrix material to the outside vascular wall. Stimulation of a device combined with a photoreactive groups, e.g., with ultraviolet light, will activate the photoreactive groups to increase adhesion.

The present invention further provides for a device comprising a thin layer of collagen which is applied to the perivascular surface of a metallic closure device. The metallic closure device may be in the form of a staple, clip, disc, or miniature clamp that may be used for vascular closure.

FIGS. 1A, 1B, 2A, and 2B illustrate embodiments of the present invention 1. FIG. 1A shows a rectangular sheet of a matrix material 2 having disbursed or distributed therein an agent 3 of the present invention (shown by stippling). FIG. 1B illustrates a further embodiment of the invention shown in FIG. 1A in which a hole 4 has been created in the drug-containing matrix material 3, 2. It will be understood by one skilled in the art that the diameter of the hole 4 will be adjusted to accommodate the outside diameter of any vascular or graft structure passing therethrough. In one embodiment, the diameter of the hole 4 is 6 mm.

FIGS. 2A and 2B illustrate a further embodiment of the present invention in which an exterior support or skeletal structure or means 5 is employed. Support 5 is exterior to the matrix material sheet 2 when the sheet 2 is rolled or coiled into a cylindrical shape. Exterior skeletal means such as PTFE and Dacron sheets are among the support materials presently contemplated. Many other such exterior skeletal support means will occur to one skilled in the art. As is shown, FIG. 2B illustrates an embodiment of the invention in which a hole 4 (which may vary in diameter) is employed.

FIGS. 3A, 3B, and 3C illustrate an embodiment of the invention employing an interlocking design in which one edge of the rectangular agent-eluting sheet or matrix material interlocks adjacent the opposite edge. More specifically, FIG. 3A shows a rectangular matrix material 2 having a therapeutic agent 3 (shown in stippling) disposed or disbursed therein. Also shown on the sheet illustrated in FIG. 3A is a series of v-shaped notches 6 located approximately adjacent one edge 7 of the agent-containing matrix material. Cooperating with notches 6 on the opposite edge 8 is a series of projections 9, which are arrow-head shaped.

However, other combinations of projections 9 and slots 6 certainly are contemplated by this invention. Thus, assembly of a sleeve embodiment of the present invention involves rolling edge 8 toward edge 7 (shown in FIG. 3B) and inserting projections 9 into slots 6. As is shown in FIG. 3C, projections 9 have been inserted into slots 6 from the inside of the tubular structure, such that the points 10 of projections 9 project from the inside to the outside of the structure. As is shown, the following edges 11 of projections 9 cooperate with v-shaped slots 6 to lock the flat structure into a cylindrical vascular-dimensioned sleeve 12.

Vascular sleeve 12 further defines a lumen 14. Lumen 14 is of a vascular dimension such that the interior surface of sleeve 12 would be in contact with the exterior surface of a vascular structure to which the sleeve 12 was attached. In this fashion, the drug or agent-eluting, vascular-dimension sleeve is deployed over and around the vascular structure with which this invention is to be used.

FIGS. 4A and 4B illustrate a second interlocking embodiment of the present invention. In this embodiment, a strip-form of the present invention is utilized. Agent-eluting sleeve 16 comprises an elongate drug or agent-eluting matrix material 17, alone or in conjunction with an external support means (not shown). Created in matrix material 17 are two locks 18 located on opposite ends thereof. Cooperating with lock 18 are windows 19 into which locks 18 are inserted, such that the sleeve 16 is deployed against and on the exterior of the operant vascular structure. As is shown in FIG. 4B, lock 18 may be inserted into window 19 from the inside toward the outside. In an alternative embodiment, lock 18 may be inserted into window 19, from the outside toward the interior of the sleeve structure. Also shown in FIG. 4A is a representative shunt opening 20 including two shunt contact wings or flaps 21.

FIG. 5 illustrates another embodiment of the present invention in which an external wire support or framework means is employed. External wire framework 20 surrounds a preferred embodiment of the present invention, i.e., a PTFE and drug-coated collagen matrix material 22 disposed around vessel 24.

FIGS. 6-13 illustrate various arterio-venous fistuale. A drug eluting sleeve or matrix material of the present invention 26 is shown to be implanted, wrapped, or placed around the various fistulae 32 shown in the several figures. In each of these figures venous structures are designated 28 and arterial structures are designated 30. Arrows 34 illustrate the direction of blood flow.

FIGS. 10-13 illustrate a further embodiment of this invention in which a graft, e.g., a PTFE graft, 36 is used in conjunction with the present invention. As is shown in FIG. 13, graft 36 may itself include a matrix material with a drug or agent 36 (shown in stippling) of this invention.

A further application of the sleeve of the present invention involves using the interior drug-imbibing protein layer as a drug source or reservoir. Accordingly, the particular drug may be replenished periodically, e.g., by puncturing the sleeve with a needle and delivering additional drug thereto or creating a reservoir for the drug within the sleeve from which it can be gradually eluted.

Figure 21:
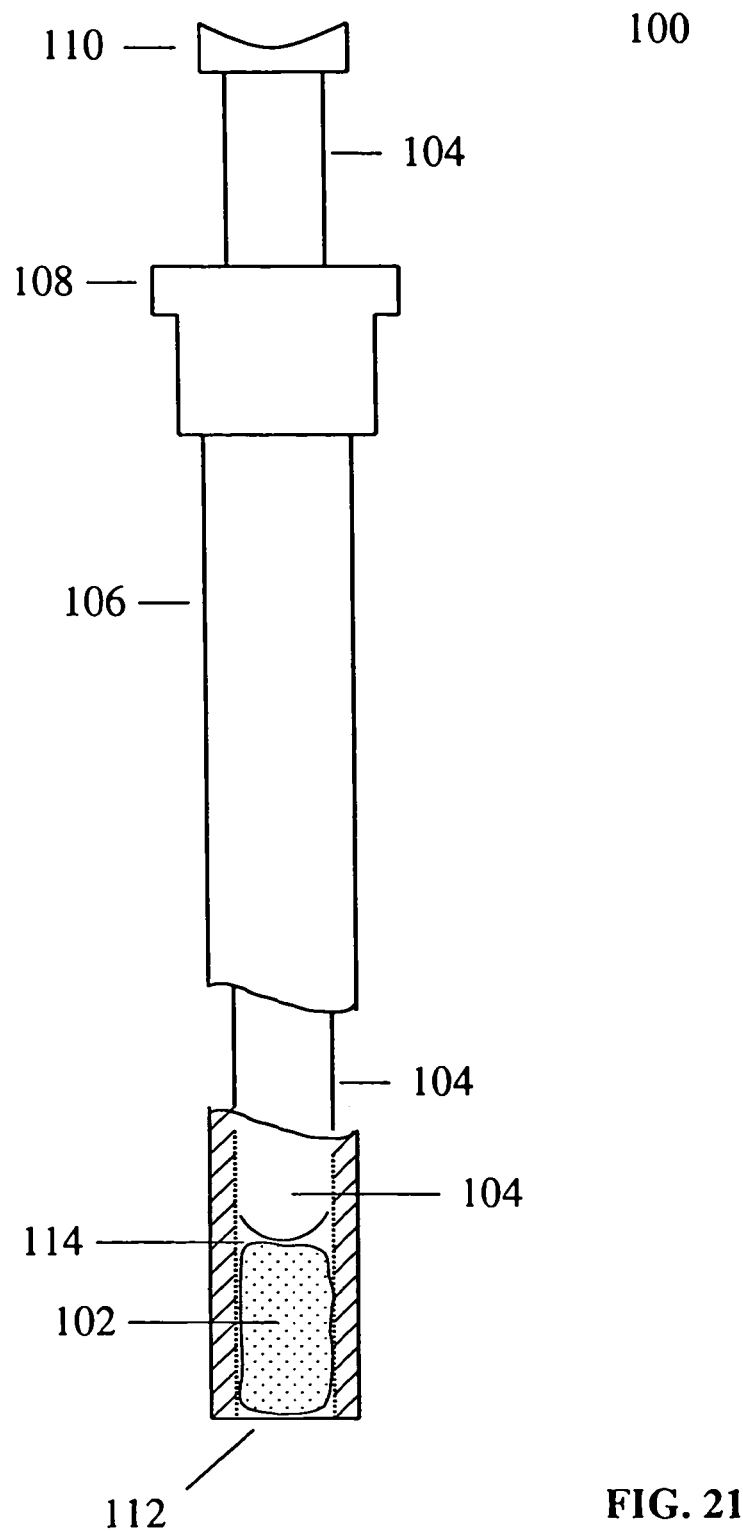
FIG. 21 illustrates an embodiment of the invention as a plug device.

Referring now to FIG. 21, in another embodiment of the present invention as a plug, a therapeutic agent may be combined with a matrix or sealant material to form a hemostatic plug composition. In a preferred embodiment, a hemostatic plug composition of collagen and rapamycin may be applied to a site of vascular compromise to seal the puncture or opening and to prevent or minimize the tissue response to the implanted matrix, e.g., inflammation and fibrosis. The composition of this embodiment may contain rapamycin in an amount of about 0.2 µg mg to about 100 mg mg per milligram weight of the hemostatic plug composition. The hemostatic plug of the present invention may comprise a combination of one or more types, e.g., chitosan, collagen, fibrin, and forms, e.g., fibers, sponge, paste, gel, sheet, of hemostatic material, as well as other therapeutic agents, e.g., anti-inflammatories, antibiotics.

FIG. 21 illustrates an embodiment of the hemostatic plug in a device. The plug device 100 generally comprises a plug of hemostatic and therapeutic material 102, a plunger or applicator 104, and a sheath 106. The sheath 106 generally comprises a tubular body defining a lumen 114, and a flange 108 disposed at the proximal end of the sheath 106. The flange 108 is designed to serve as a grip for the index and middle fingers (not shown). The sheath 106 may be composed of a pliable biocompatible material suitable for use in surgical procedures and is preferably composed of a durable plastic material.

The outer diameter of the sheath 106 and the inner diameter of the lumen 114 are designed to permit sliding movement, with a close fit, of the plunger or applicator 104 disposed within the sheath 106. In the preferred embodiment, the outer diameter of the sheath 106 is in the range of about 3 to about 10 mm. However, this diameter may vary according to the procedural needs, as will be readily appreciated by those skilled in the art.

The plunger or applicator 104 generally comprises a cylindrical body and a thumb plate 110 disposed at its proximal end. The plunger or applicator 104 will generally be composed of a pliable biocompatible material suitable for use in surgical procedures and is preferably composed of a durable plastic material. The size of the outer diameter of the plunger or applicator 104 is selected to be slightly less than the size of the inner diameter of the lumen 114 to permit sliding passage. In the preferred embodiment, the plunger or applicator 104 has a blunt distal end for engaging and advancing the hemostatic plug 102 through the sheath 106 and out the outlet 112.

To use the plug device, the medical personnel positions the distal end of the sheath 106 at the vascular puncture site and applies pressure to the thumb plate 110 of the plunger or applicator 104. As the plunger or applicator 104 slides through the sheath 106, it advances the hemostatic plug 102 until it exits from the sheath 106 through the outlet 112. The length of the sheath 106 and the plunger or applicator 104 may be selected so that when the thumb plate 110 of the plunger or applicator 104 abuts the flange 108 of the sheath 106, the medical personnel knows that the plug 102 has been pushed entirely out of the lumen 114. The hemostatic plug 102 may be mechanically held against the site of puncture or opening to achieve immediate hemostasis. The hemostatic material will begin to interact with bleeding tissue to maintain hemostasis without mechanical pressure. An example of a device that can be used with the present invention is disclosed in U.S. Pat. No. 5,310,407 (Casale).

Figure 22:
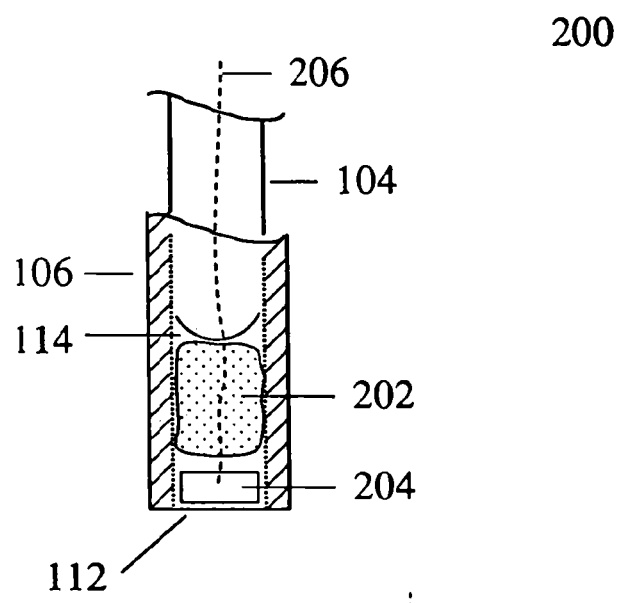
FIG. 22 illustrates an alternative embodiment of the plug device, detailed distally.

An alternative embodiment of the plug of the present invention is shown in FIG. 22. In the alternative plug device 200, the plug of hemostatic and therapeutic material 202 may be connected to a sealing member 204 that is located distally within the sheath 106 and adjacent to the sheath outlet 112. The sealing member 204 comprises a highly absorbent and compressed material, such that it swells when deployed and comes into contact with fluids such as blood, and is also preferably composed of a biodegradable material. The sealing member 204 may also comprise hemostatic and therapeutic materials, such as collagen and rapamycin.

Attached to the sealing member 204 is a filament 206 that extends through the plug 202 and the plunger or applicator 104 and exits the plug device. The filament 206 is preferably composed of a flexible, biodegradable material. To seal a vascular puncture or opening, the plug is introduced into the artery or puncture until the plug device 200 reaches the target location within the artery. The plunger or applicator 104 disposed within the plug device 200 is operated to expel the plug 202 and sealing member 204. The plug device 200 and plunger or applicator 104 may then be removed to leave the filament 206 still attached to the plug 202 and sealing member 204.

The medical personnel may then pull on the filament 206, to pull the sealing member 204 toward the puncture or opening (not shown) until the sealing member 204 engages the puncture or opening. The sealing member 204 effectively seals the puncture or opening in the vasculature, and the plug 202 extends through and seals the length of the puncture or opening in the tissue adjacent to the vasculature. The filament 206 may be secured outside the body by a tape (not shown) or other securing means. An example of a device that can be used with the present invention is disclosed in U.S. Pat. No. 4,890,612 (Kensey).

The collagen matrix component of devices used to seal vascular punctures, i.e., to obtain hemostasis, can provoke tissue responses such as immunologically mediated allergic reactions, fibrosis, infection, inflammation thrombosis and granulomas. Some or all of these tissue responses can render future access of the blood vessel difficult or impossible. Therefore, the hemostatic plug of sealant matrix and therapeutic agent as in the present invention may be advantageously used to seal vascular punctures and to simultaneously reduce the tissue response to the collagen matrix.

The matrix in a hemostatic plug of the invention may contain collagen, fibrin, chitosan, or other similarly functioning components useful as a biological sealant. A variety of therapeutic agents may be combined, alone or together, with the collagen matrix, such as antibiotics, anti-inflammatories, antiproliferatives, hormones, or steroids, as described above. In addition, the matrix and therapeutic agent composition may further include adjuvants or excipients, such as agents that inhibit accumulation of the matrix material in the vasculature or reduce calcification of the vasculature.

Figure 23:
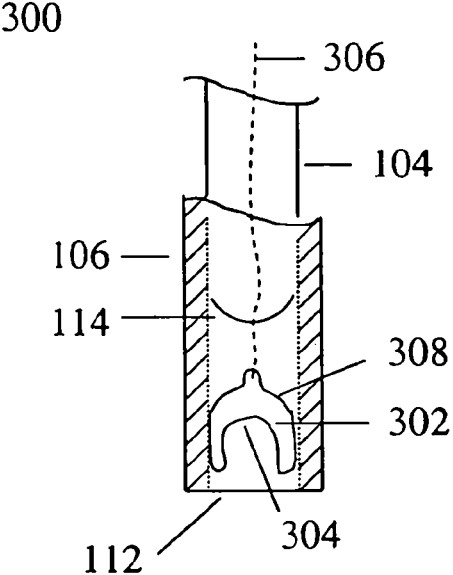
FIG. 23 illustrates an embodiment of the invention as an anchor device, detailed distally.

Referring now to FIG. 23, in another embodiment, the present invention provides an anchor device 300 to seal vascular punctures and to simultaneously reduce the tissue response to the foreign material used to seal the puncture. In lieu of a plug, an anchor 302 is attached to the plunger or applicator 104 by a filament 306 and disposed within the lumen 114 of the sheath 106 at the distal end. The anchor 302 is preferably composed of a resilient, biodegradable material, e.g., gelatin, and optionally composed of or coated with hemostatic material or a therapeutic agent or both. The filament 306 is preferably composed of a flexible, biodegradable material. The proximal end of the filament 306 is located external to the anchor device 300 and accessible to medical personnel operating the anchor device 300.

Figure 24:
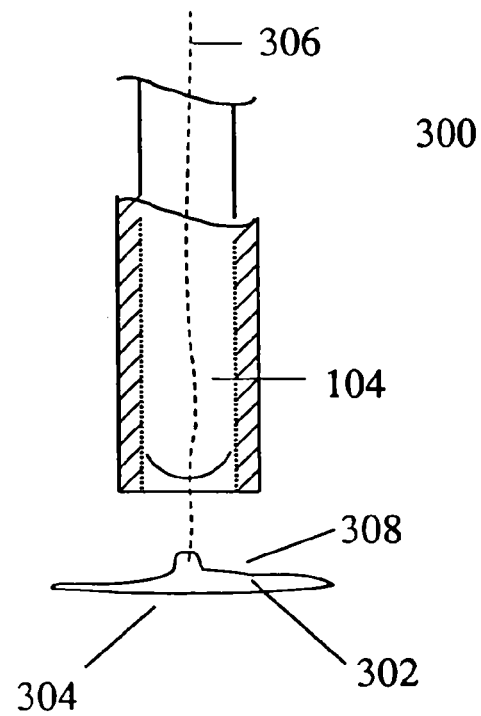
FIG. 24 illustrates the anchor device when deployed.

When disposed within the sheath lumen 114, the anchor 302 is in a constrained or compressed configuration, and when unconstrained or expanded outside the sheath 106, the anchor 302 assumes an enlarged configuration, e.g., in the shape of a disc, as shown in FIG. 24. The anchor 302 should be relatively thin so as not to obstruct bloodflow within the vessel being treated. The distal surface 304 of the anchor 302 expands into a relatively flat surface, as does the proximal surface 308, which can engage the interior of an artery or vein (not shown) to seal off the puncture site.

To seal a puncture site, the filament 306 that is connected to the anchor 302 may be pulled so as to pull the anchor 302 toward the puncture site until its proximal surface 308 contacts the inner surface of a vessel. This establishes a hemostatic seal of the puncture, and in a preferred embodiment, the therapeutic agent imbibed matrix material will elute the agent to also prevent, suppress, or treat smooth muscle proliferation. The filament 306 may be secured outside the body by a tape (not shown) or other securing means for a time sufficient to confirm hemostasis. An example of a device that can be used with the present invention is disclosed in U.S. Pat. No. 4,852,568 (Kensey).

Figure 25:
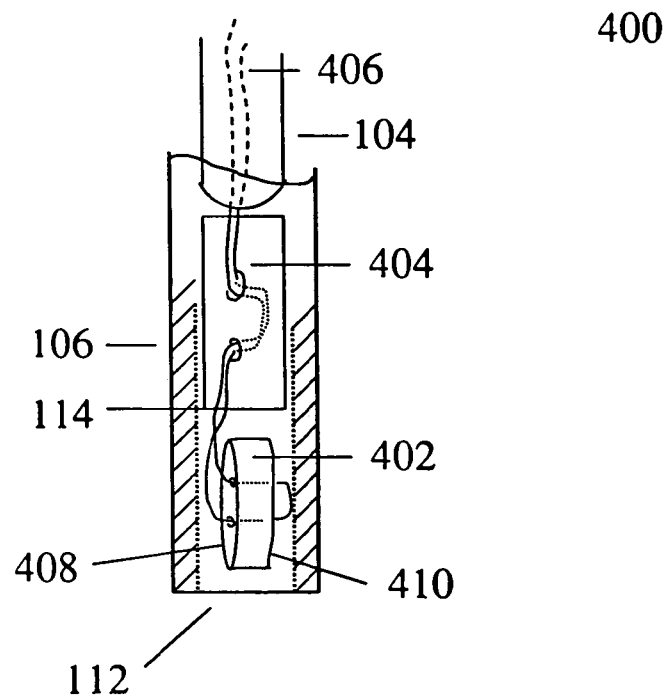
FIG. 25 illustrates an embodiment of the invention as a sandwich device, detailed distally.
Figure 26:
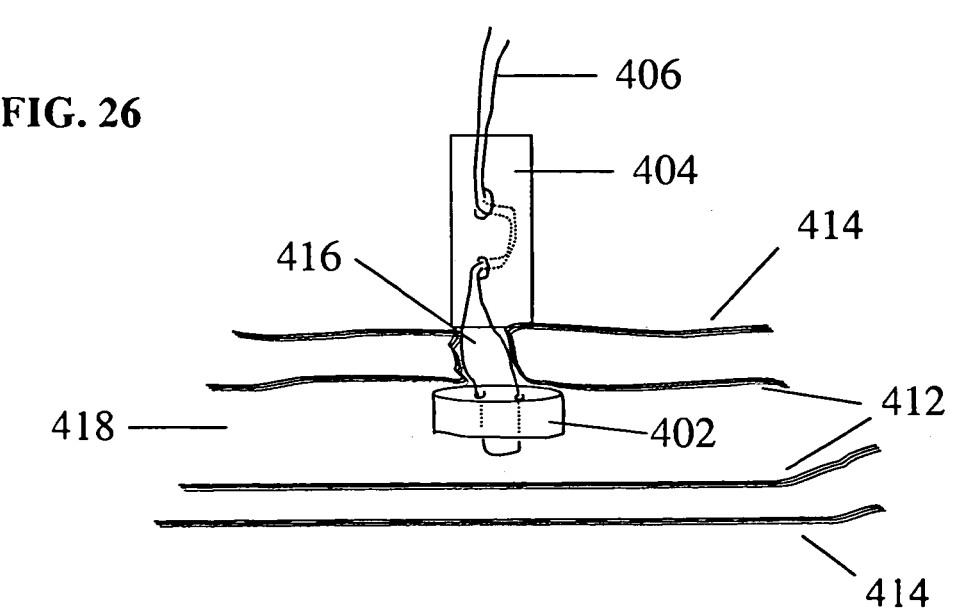
FIG. 26 illustrates the sandwich device when deployed.

Referring now to FIG. 25, in another embodiment of the present invention as a sandwich device 400, the anchor 402 and sealing member 404 are disposed within the sheath lumen 114 and connected to each other and to the plunger or applicator 104 by a filament 406. To effect a seal using the device 400, the medical personnel inserts the sheath 106 through the vascular puncture or incision 416 and expels the anchor 402 through the outlet 112 and into the vascular lumen 418 by operating the plunger or applicator 104. The medical personnel then manipulates the filament 406 to pull the anchor 402 toward the puncture site 416 until it engages with the inner surface of the vascular wall 412 as in FIG. 26. Again manipulating the filament 406, the medical personnel pulls the sealing member 404 into engagement with the outer surface of the vascular wall 414, as shown in FIG. 26. The anchor 402 and sealing member 404 thus engage the vascular tissue around the puncture 416 in a sandwich configuration, as shown in FIG. 26, and seal the site.

In FIG. 25, the anchor 402 is depicted as a disc disposed vertically so that its two flat surfaces 408, 410 are parallel to the sheath 106 and located adjacent to the outlet 112. The sealing member 404 sits proximal and adjacent to the anchor 402 within the sheath lumen 114. The sealing member 404 may be tubular or cylindrical. The filament 406 loops through the anchor 402 and sealing member 404 and continues through the plunger or applicator 104 to the outside of the body and is accessible to medical personnel. The plunger or applicator 104 of this device may optionally incorporate means to visually or audibly indicate the proper operation of the device. U.S. Pat. No. 5,021,059 (Kensey et al.) discloses an example device as well as visual and audible indicator means that can be used with the present invention.

The anchor 402 may be composed of a resilient, biodegradable material such as gelatin, and preferably also composed of or coated with hemostatic materials, therapeutic materials, or both. The anchor 402 should be sufficiently thin or flat so as not to obstruct bloodflow when deployed within the interior of a vessel. In a preferred embodiment, the anchor 402 approximates the thickness of a vessel wall and comprises collagen and rapamycin (or other therapeutic agent(s)).

The sealing member 404 may be composed similarly but is preferably larger and more bulky than the anchor 402 so as to exert an expelling force on the anchor 402 during operation of the device. The cylindrical body of the sealing member 404 may resemble the plug shown in FIGS. 21 and 22 and may be composed of similar hemostatic materials, e.g., chitosan, collagen, fibrin, and therapeutic agents, e.g., antiproliferatives, antibiotics, anti-inflammatories. Importantly, both the sealing member 404 and anchor 402 should be resilient or firm enough to hold the filament 406 in place as shown in FIGS. 25 and 26. The filament 406 is preferably composed of a flexible, biodegradable material.

All of the foregoing devices may comprise any or the aforementioned therapeutic agents, and may comprise multiple layers with varying drug densities or doses. For example, an outer layer in immediate contact with the vascular tissue may comprise a drug with kinetics designed for rapid release, and an inner layer not in contact with the vascular tissue may comprise a drug with kinetics designed for slower or extended release of the therapeutic agent. Alternatively, all of the foregoing devices may comprise synergistic layers. For example, the outer layer may comprise one type of drug, e.g., an antiproliferative agent, while the inner layer may comprise another type of therapeutic agent, e.g., an antibiotic agent.

To illustrate further, one therapeutic agent may be used for immediate release of rapamycin from the collagen matrix, which has large pores ranging from about 0.001-100 μm. A second therapeutic agent may be used for extended release of dexamethasone from the fibrin matrix, which has small pores ranging from about 0.001-0.004 mμ. Thus, for example, an outer layer of a device of the invention may comprise rapamycin imbibed in a collagen matrix, and an inner layer may comprise dexamethasone imbibed in a fibrin matrix. The outer layer of collagen matrix will rapidly elute rapamycin for immediate treatment of any vasculoproliferative responses after a procedure, and the inner layer of fibrin matrix should more slowly elute dexamethasone and/or antibiotics to counteract any inflammation and or infection over an extended period of time.

G. Conditions and Diseases Treated Using the Invention

The present invention may be applicable to vascular diagnostic and interventional procedures including but not limited to angiography, atherectomies, angioplasty, stent implantation, rotablators, thrombolysis therapy, laser angioplasty, valvuloplasty, aortic prosthesis implantation, intra-aortic balloon pumps, pacemaker implantation, dialysis, electrophysiology, and procedures relating to percutaneous extracorporeal circulation. The present invention may be used in both adults and children independent of the age of the vessel to be sealed. In addition, multiple therapeutic agents, including antibiotics, anti-inflammatories, hormones, or steroids, may be combined with the sealant matrix, which itself may be composed of more than one matrix material.

H. Combination Therapy

The methods, compositions, and devices of the present invention may be practiced in conjunction with standard or other therapies indicated for the condition or disease to be treated. For example, the invention may be practiced percutaneously or surgically, while the adjunct therapy may be administered by any appropriate route, including, but not limited to, oral, intravenous, intramuscular, subcutaneous, percutaneous, or mucosal. The therapies may be combined to produce synergistic effects.

"Combination therapy" refers to the administration of therapeutic or pharmacological agents in a sequential or substantially simultaneous manner. "Combination therapy" also refers to the administration of the therapeutic agents described herein in further combination with other pharmacologically active ingredients, or to the practice of the present invention in further combination with other methods or devices.

I. Examples

The following examples are set forth to illustrate the device and the method of preparing matrices for delivering therapeutic agents. The examples are set forth for purpose of illustration and not intended to limit the present invention.

Example 1

Inhibitory Effect of Different Antiproliferative Agents

Prefabricated collagen matrices were placed in different antiproliferative drug solutions until complete saturation occurred. The antiproliferative drugs were chosen to represent the more active compounds capable of smooth muscle cell and fibroblast inhibition without inhibiting collagenase and elastase, which enzymatically inhibit collagen accumulation—one cause of restenosis. The collagen matrices were saturated with these compounds at a concentration of 25 µg/ml lyophilized, washed with 0.066 M phosphate buffer of pH 7.4 at 37° C. for 24 hours and cut in the shape of a disc with density of compound of about 5 µg/cm$^2$. After washing, sterile discs 15 mm in diameter were placed in a 24-well culture plate, and cells were seeded at a density of 5,000/cm$^2$. Five days later, cell number was counted and enzymatic activity evaluated in the aliquots of media by chromogenic substrate hydrolysis and spectrophotometry. Among the tested agents in this comparative in vitro test, paclitaxel and rapamycin (sirolimus) performed similarly. These data are presented in Table 2.

TABLE 2

Inhibitory Effect of Different Antiproliferative Agents

| Agent | SMC Inhibition % | Fibroblast Inhibition % | Collagenase Activity % | Elastase Activity % |
|---|---|---|---|---|
| Control (plain matrix) | 0 | 0 | 100 | 100 |
| Actinomycin D | 44 ± 11 | 35 ± 8 | 55 ± 9 | 84 ± 11 |
| Cyclosporin A | 61 ± 7 | 53 ± 7 | 104 ± 5 | 87 ± 7 |
| Methotrexate | 32 ± 9 | 28 ± 6 | 23 ± 12 | 14 ± 3 |
| Paclitaxel | 88 ± 6 | 62 ± 11 | 98 ± 5 | 90 ± 4 |
| Rapamycin | 94 ± 5 | 90 ± 12 | 137 ± 8 | 142 ± 5 |
| Tetracycline (free base) | 11 ± 8 | 13 ± 5 | 56 ± 8 | 81 ± 4 |

Example 2

Capacity of Different Types of Matrices to Bind Rapamycin

In the next in vitro study, the ability of different matrices to bind rapamycin (sirolimus) was tested. A prefabricated collagen matrix (BioMend from Sulzer Calcitek, Inc., Carlsbad, Calif. or BIOPATCH containing collagen-alginate from Ethicon, Inc., Somerville, N.J.) with rapamycin (sirolimus) was prepared as described in Example 1 at an initial rapamycin (sirolimus) concentration of 250 µg/ml. Prefabricated chitosan (using the technique described in Aimin et al., Clin. Orthop. (1999), 366: 239-247) and fibrin matrices (using the technique mentioned in Example 5) were also placed in 250 µg/ml of rapamycin (sirolimus) in dimethylsulfoxide (DMSO) solution until complete saturation occurred. After solvent evaporation, the matrices combined with drugs were washed with 0.066 M phosphate buffer of pH 7.4 at 37° C. for 24 hours.

To compare matrix capacity, fluorescent rapamycin (sirolimus) derivate loaded onto 1.88 cm$^2$ matrix surface of the same thickness was used. After incubation with 0.14 M NaCl solution, the residual rapamycin (sirolimus) was extracted with DMSO, and yield was measured using fluorescence spectroscopy. As expected, capacity of protein matrices was found to be higher than the polysaccharide chitosan matrix. Usefulness of fibrin or collagen as matrix for antiproliferative drug delivery may depend on a particular combination or additional components or requirements of longevity of the matrix. These data are presented in Table 3.

TABLE 3

Matrix Capacity for Rapamycin

| Matrix | Rapamycin Binding Capacity (µg/cm$^2$) |
|---|---|
| Chitosan | 78.7 ± 8.9 |
| Collagen | 124.5 ± 14.3 |

TABLE 3-continued

Matrix Capacity for Rapamycin

| Matrix | Rapamycin Binding Capacity (µg/cm²) |
|---|---|
| Collagen-alginate | 131.1 ± 12.3 |
| Fibrin | 145.8 ± 12.7 |

Example 3

Delivery Systems Using Liposomes

Liposomes represent a form of drug delivery system and offer controlled release of biologically active agents. They are used in pharmaceutical formulations, especially for water insoluble drugs, e.g., rapamycin. Liposomal entrapment has been shown to have considerable effect on the pharmacokinetics and tissue distribution of administered drugs. The formulations tested included nonionic liposomal formulation composed of glyceryl dilaureate, cholesterol, and polyoxylene-10-stearyl (all from Sigma-Aldrich Corp.) either at a weight ratio of 56:12:32 (Formulation 1) or nonionic 40% hydroalcoholic oil-in-water liposomal emulsion containing isopropyl myristate and mineral oil (both from Sigma-Aldrich Corp.) (Formulation 2).

Rapamycin was entrapped into each formulation at a concentration of 250 µg/ml in DMSO or isopropanol, and formed liposomes were applied on the surface of prefabricated collagen sheets to create maximal surface density of rapamycin. Samples were washed with 0.066 M phosphate buffer of pH 7.4 at 37° C. for 24 hours. To compare matrix capacity, liposomes loaded with fluorescent rapamycin derivate placed onto 1.88 cm² disc was used. After incubation with 0.14 M NaCl solution, matrices with remaining rapamycin were extracted with DMSO, and fluorescent yield was measured. As data presented in Table 5 indicates, liposomal delivery systems do not have significant advantages over saturated collagen matrix in ability to bind rapamycin. However, the liposomal approach may be useful for other antiproliferative drugs.

TABLE 4

Liposomal Delivery System

| Liposome | Rapamycin Binding Capacity (µg/cm²) |
|---|---|
| Nonionic cholesterol liposomes (Formulation 1) | 117.4 ± 10.9 |
| Nonionic oil-in-water emulsion (Formulation 2) | 89.6 ± 7.5 |
| Saturated collagen matrix (DMSO) | 124.5 ± 14.3 |
| Saturated collagen matrix (isopropanol) | 105.6 ± 9.7 |

Example 4

Preparation of a Laminated Collagen Film

To prepare a textured, surface-neutralized, laminated collagen film, an isotonic suspension of insoluble fibrillar collagen was obtained. Three liters of chilled collagen suspension at a concentration of 5-18%, preferably 12%, was swollen overnight in 0.3-0.6 M acetic acid, preferably 0.52 M, at 4° C. The swollen suspension was dispersed with 3 liters of crushed ice for 10-20 minutes, preferably 12 minutes, in a blender and thereafter homogenized for 30 minutes in an Ultra-Turrax® (Alfa Laval AB, Sweden). The resulting slurry was filtered through a series of filters (Cellector® from Bellco, UK) with pore sizes decreasing from 250-20 µm, mounted in filter holder (Millipore Corp., Billerica, Mass.). After degasation at 0.04-0.09 mbar, preferably 0.06 mbar, the slurry was mixed with 2 liters of chilled 0.1-0.05 M NaOH, and the final pH adjusted to 7.4±0.3.

The neutralized suspension can be stored at 4-6° C. only for several hours prior to matrix formation. This neutralized suspension serves as a foundation for preparation of a saturated or dispersed form of a matrix containing rapamycin (sirolimus). The neutralized slurry may be directly cast as a wet film with a thickness of 3 mm on a flat hydrophobic surface at room temperature. A dry film with a thickness of approximately 60-70 µm is formed. Three to five milliliters of slurry cover an area of 10 cm². On top of such a surface, several layers may be formed. The layers will serve as a basis for preparation of a saturated form of an antiproliferative agent by immersing the collagen film into solutions of rapamycin, paclitaxel, or mixtures thereof. Simultaneous combination of neutralized slurry and rapamycin or other agents in suspension may be used for preparation of film with dispersed form of active ingredients.

An important factor in the preparation of the matrix material is the porosity of the protein carrier from which the device is to be formed, since porosity controls the kinetics of drug release. Porosity may be regulated by drying rate, temperature, and the characteristics of the initial collagen. The matrix should be sufficiently porous to bind small molecules such as rapamycin (mol wt 914.2) and durable enough to maintain the shape of device. Samples of collagen matrix with effective pore sizes of 0.002-0.1 µm were tested. Higher capacity to bind rapamycin (sirolimus) in saturation experiments was observed with the matrix having pore sizes of 0.004 µm.

In addition, collagen matrices with bigger pore sizes are fragile. Since the binding capacity of the matrix for the antiproliferative agent is critical for this application, three different concentrations of rapamycin were used to prepare a rapamycin-collagen matrix combination from commercially available collagen prepared at optimal density of pores. The three different concentrations labeled high, medium, and low were 120±5 µg/cm², 60±4 µg/cm², and 30±3 µg/cm², respectively. None of these matrices were fragile or had non-uniform rapamycin (sirolimus) distribution. Different densities permit regulation of the kinetics of drug release.

Example 5

Preparation of an Implantable Fibrin Matrix Device Combined with an Antiproliferative Agent In general, to make a device based on a fibrin matrix loaded with an antiproliferative agent, aqueous fibrinogen and thrombin solutions are prepared as described below. Commercial fibrinogen can be acquired from such vendors as Sigma-Aldrich Corp., American Red Cross (Washington, D.C.), or can be prepared from plasma by well-known techniques. Alternatively, fibrinogen prepared by recombinant methods is suitable for use. Commercial active thrombin can be acquired from Sigma-Aldrich Corp. or from Johnson & Johnson (New Brunswick, N.J.) as topical USP thrombin or Thrombogen. To make the fibrinogen and thrombin solutions used to prepare the matrix, the necessary components are measured, weighed, and dissolved in about 900 ml of deionized water. Tables 5 and 6 disclose preferable compositions used to prepare fibrinogen and thrombin solutions, respectively, to prefabricate the matrix.

TABLE 5

Fibrinogen Solution Composition

| Component | Composition Range (g/liter) | Composition Preferred (g/liter) |
|---|---|---|
| Caprylic Acid | 10-35 | 18.7 |
| Fibrinogen | 50-120 | 76 |
| Glycerol | 20-80 | 40.5 |
| Heparin | 0.5-6 | 2.38 |
| TRIS buffer | 3-25 | 12.1 |
| Triton X-100 | 2-8 | 5.4 |

TABLE 6

Thrombin Solution Composition

| Component | Composition Range (g/liter) | Composition Preferred (g/liter) |
|---|---|---|
| Albumin | 1-100 | 50 |
| $CaCl_2$ | 50-250 mg/liter | 123 mg/liter |
| Factor XIII | 1,000-5,000 units | 2,500 units |
| Thrombin | 5,000-100,000 units | 8,000 units |
| Troglitazone | 3-24 | 8 |

The glycerol in Table 6 is used as a plasticizer. Other plasticizers would also be suitable for the present invention. TRIS buffer is used for pH adjustment. Suitable alternatives for TRIS include HEPES, Tricine, and other buffers with a pKa between 6.8 and 8.3. Triton X-100 is a non-ionic detergent and stabilizer and may be substituted by other detergents and stabilizers. Caprylic acid may be substituted by other agents that provide protection from denaturation, e.g., alginic acid. Fibrinogen converted to fibrin is the most critical reagent in the matrix because it controls the material properties of the matrix, such as flexibility, pore size, and fiber mass density. These features determine how easily other molecules can diffuse within the matrix and how long the matrix may remain intact before it is resorbed.

In Table 7, albumin is a stabilizer of thrombin. Thrombin controls the rate of fibrin matrix formation. The presence of Factor XIII is preferred but not necessary. Factor XIII covalently cross-links fibrin, making the matrix more stable. Calcium ions are needed for activation of thrombin. Troglitazone (Sankyo, Japan) is a thiazolidinedione derivative that decreases collagen accumulation in the vascular wall (Yao et al., *Heart* (2000) 84: 209).

It is preferable to completely dissolve each component before adding the next component. If necessary, after the last component is dissolved, the pH is adjusted to 7.0-7.4 and the solution volume adjusted to 1 liter with water. The solutions are then degassed. Both solutions are dispensed by pump through a mixture chamber onto a non-stick, preferably hydrophobic, surface to form a film approximately 2 mm thick. The film is then dried for about 3-6 hours at a temperature in the range of about 20-60° C., at a pressure of about 30 torr. Residual moisture of the film is about 10%, preferably less than 3%, of the total wet weight.

On this surface, dry solid rapamycin is added to create density in the range of 100-500 µg/cm² of film. A second layer of fibrin matrix is formed on top of this surface, such that the drug is sandwiched between the two layers of fibrin. In one embodiment of the present invention, one would add an antiproliferative or antirestenotic agent like rapamycin or taxol, an antirejection drug like rapamycin or tacrolimus, an anti-inflammatory drug, or an antisense oligonucleotide to enhance antirestenotic effects. These solid materials would be added to supplement the fibrin-rapamycin sandwich complex described above.

Example 6

Method of Cross Linking Chitosan Matrix

To increase the binding capacity of a chitosan matrix for an antiproliferative drug, fibers may be cross-linked. Fifty milliliters of chilled chitosan suspension at a concentration from 10-25%, preferably 12%, were gently and slowly mixed with 5-25 ml of acrylic acid chloranhydride for 30 minutes to acetylate this polymer. After this time period, a solution of rapamycin in DMSO at a concentration of 250 µg/ml was added, mixed vigorously, and poured onto the chitosan matrix surface for spontaneous cross-linking and formation of conjugated rapamycin. Because of the microporous structure of the chitosan, this approach allows an increase in the binding capacity of the matrix from 15-45%.

Example 7

Incorporation of Rapamycin into Collagen Matrix by Dispersion, Immobilization, and Immobilization-Dispersion Besides the technique of saturation, rapamycin was incorporated into the collagen matrix by three other methods: dispersion, immobilization, and immobilization-dispersion.

Dispersion technique: An aqueous slurry of water insoluble collagen was prepared using non-crosslinked dry, highly purified, lyophilized calfskin collagen obtained from Elastin Products Co. (Owensville, Mo.). This collagen and solubilizing buffer are chilled to a temperature of 2-8° C., preferably 4° C., and vigorously mixed to prepare collagen slurry containing 10-21%, preferably 12%, of collagen protein. Such slurry includes 9% of plasticizer, glycerol, 15% of rapamycin in DMSO at a concentration of 250 µg/ml, and water. The solution had a viscosity of 50,000 cps.

Immediately after mixing with rapamycin (sirolimus), 8% glutaraldehyde is added to the slurry (100-350 ml/liter of slurry). The aqueous slurry must be homogenous and degassed, and the pH adjusted to 6.0-7.1. The solution is constantly and vigorously mixed and dispersed by pump onto a non-stick surface to form a film approximately 2 mm thick. All procedures are carried out at a temperature of 4° C. The film is then dried for about 3-7 hours at temperatures in the vicinity of 45° C., and a pressure of 15 ton until its residual moisture is less than about 10% of the total weight. The drug solution application and drying steps are repeated three more times.

Immobilization technique: The same collagen preparation from Elastin Products Co. is used. One volume of 12% collagen slurry is chilled and coupled with rapamycin (sirolimus) by esterification of an antiproliferative drug. Esterification is carried out with 0.9 M N-hydroxysuccynimide (Pierce Biotechnology, Inc., Rockford, Ill.) in the presence of 0.9 M N-dicyclohexylocarbodimide (Pierce Biotechnology, Inc.) at 2-4° C. for two days. Conjugates are prepared by titration of active N-hydroxysuccynimide ester of rapamycin (sirolimus)

in DMSO under the surface of stirred collagen suspension. The pH of the reaction is maintained between 7.0-8.5, preferably 7.8.

After drying, the films with conjugated rapamycin (sirolimus) are washed with 0.15 M NaCl containing 0.02 M sodium bicarbonate at a pH of 7.4. HPLC reveals no free rapamycin (sirolimus) in the matrix. Rapamycin (sirolimus) ester reacts with amino- or hydroxyl-groups of amino acid residues forming a covalent linkage with collagen. After such immobilization, rapamycin (sirolimus) is released as a result of in vivo or in vitro degradation-erosion of the matrix. Nakano et al. make reference to collagen (SM-10500) degradation and resorption by a natural metabolic process in Rhesus monkeys during six months (Nakano et al., *Kisoto Rinsho* (*Clinical Report*) (1995) 29: 1675-1699).

To study the rate of rapamycin release from the matrix, samples are washed with 0.066 M phosphate buffer of pH 7.4 at 37° C. for 24 hours and cut into discs with an area of 1.88 cm$^2$, and placed into a 24-well culture plate containing 0.14 M NaCl, 0.05M Tris buffer, 0.5% of albumin, and 0.1 mg/ml collagenase, at pH 7.0. Collagenase is added to increase erosion of the collagen matrix and to facilitate release of rapamycin. Aliquots are collected at various time intervals from the wells. A combination of dispersed and conjugated forms is also prepared. In all these forms, the content of rapamycin is 5.0 µg/cm$^2$. The samples are placed in wells and 1 ml of elution media containing serum are added. Aliquots are taken every hour.

Figure 14:
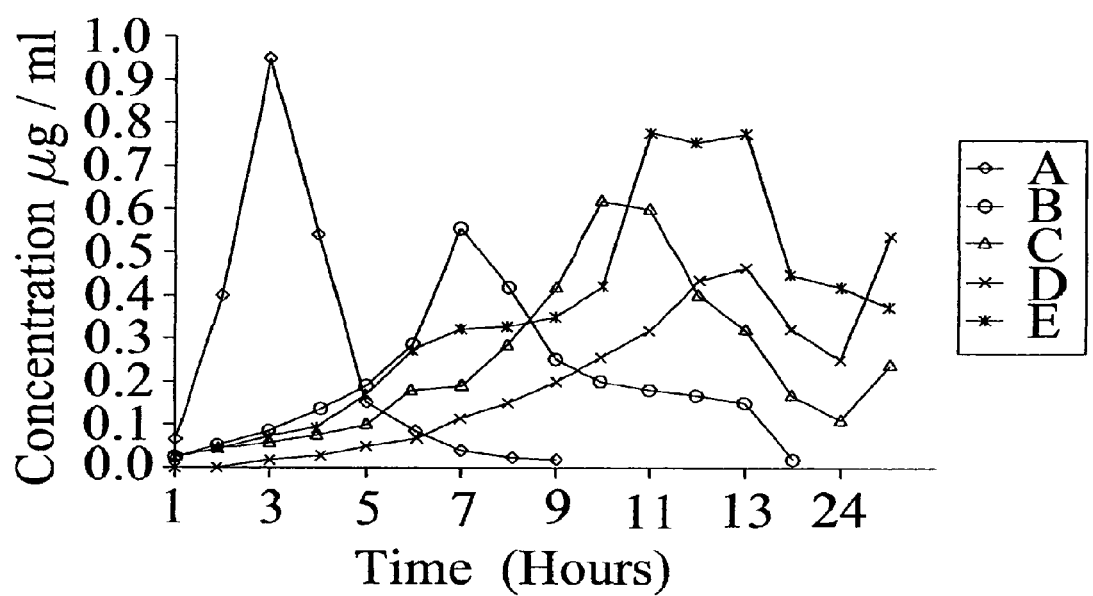
FIG. 14 shows rates of release of collagen saturated with rapamycin (sirolimus) and tetracycline.

The content of rapamycin is measured according to the procedure of Ferron et al. (Ferron et al., J. Chromatogr. B. Biomed. Sci. Appl. (1997) 703: 243-251). These measurements are made using batch assay and, therefore, represent release rates at 0 ml/min flow rate. The results are tabulated in Table 7 and graphically illustrated in FIG. 14. Concentrations of the antiproliferative drug are in µg/ml.

for less soluble rapamycin, this peak is delayed (about seven hours). It has been shown in experiments in vitro that collagen saturated with soluble antibiotics such as gentamicin, cefotaxin, tetracycline, or clindamycin delivers these antibiotics at effective concentrations for four days (Wachol-Drewek et al., *Biomaterials* (1996) 17: 1733-1738). Other laboratories have shown in vivo that collagen saturated with gentamycin at a concentration of 3 µg/g and implanted into muscle tissue is capable of delivering antibiotic into blood through day 28. However, concentration was less than optimal (Mehta et al., *J. Orthop. Res.* (1996) 14: 749-754).

Theoretically, given the low concentration of collagenase in perivascular space and the low flow rate of perivascular fluid (only a few milliliters per day), a matrix material saturated with rapamycin might produce in vivo delivery kinetics, which will support effective local concentration of an antiproliferative drug for a period of several weeks to prevent and combat progress of smooth muscle cell proliferation. Inhibitory concentrations for smooth muscle cell would be in the range of 0.001-0.005 µg/ml culture media. Such levels are met or exceeded in vitro for three weeks. Moreover, rapamycin dispersed into collagen matrix may exhibit an antiproliferative effect for a month or longer. Finally, conjugated and combined forms may support treatment until complete matrix erosion.

Example 8

Biological Activity of Rapamycin in the Rapamycin-Collagen Matrix

The most important parameter when assessing the combination of rapamycin and collagen is inhibition of smooth

TABLE 7

Rate of Release of Collagen Saturated with Tetracycline and Rapamycin (rapamycin combined with collagen matrix using four different methods)

| | Drug Concentration (µg/ml) | | | | |
|---|---|---|---|---|---|
| Time (hours) | Collagen Saturated with Tetracycline | Collagen Saturated with Rapamycin | Rapamycin Dispersed throughout Collagen | Collagen Conjugated with Rapamycin | Combination of Dispersed and Conjugated Forms |
| 1 | 0.06 | 0.01 | 0.01 | 0 | 0.01 |
| 2 | 0.40 | 0.05 | 0.03 | 0 | 0.02 |
| 3 | 0.96 | 0.09 | 0.06 | 0.01 | 0.07 |
| 4 | 0.54 | 0.15 | 0.08 | 0.02 | 0.09 |
| 5 | 0.15 | 0.19 | 0.12 | 0.05 | 0.17 |
| 6 | 0.08 | 0.28 | 0.18 | 0.07 | 0.26 |
| 7 | 0.02 | 0.57 | 0.19 | 0.11 | 0.31 |
| 8 | 0.01 | 0.44 | 0.29 | 0.13 | 0.32 |
| 9 | 0.01 | 0.24 | 0.41 | 0.19 | 0.34 |
| 10 | — | 0.20 | 0.62 | 0.27 | 0.41 |
| 11 | — | 0.19 | 0.61 | 0.31 | 0.78 |
| 12 | — | 0.18 | 0.40 | 0.42 | 0.76 |
| 13 | — | 0.15 | 0.32 | 0.45 | 0.79 |
| 14 | — | 0.02 | 0.16 | 0.32 | 0.45 |
| 24 | — | — | 0.11 | 0.24 | 0.42 |
| Totally Dissolved Matrix | 0 | 0.003 | 0.23 | 0.53 | 0.39 |

Figure 15:
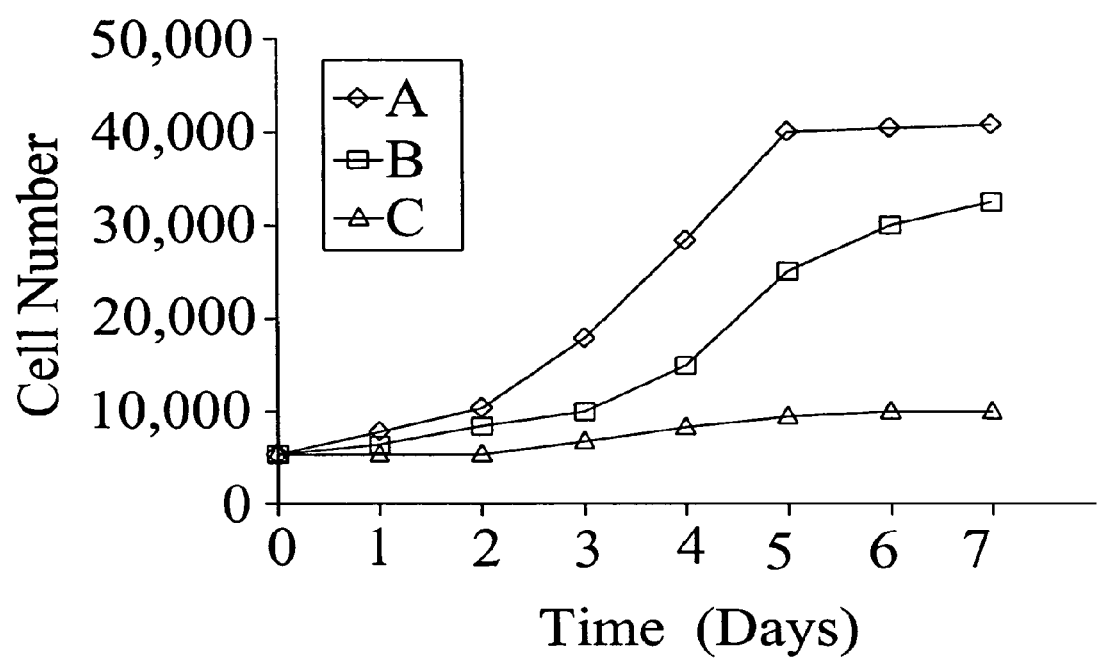
FIG. 15 is a comparison of inhibition of growth of smooth muscle cells using collagen matrices combined with different antiproliferative agents.

These data show that different forms of drug imbedding and drugs with different solubility have distinct kinetics. In the case of comparatively soluble tetracycline, after saturation of the collagen matrix with the free base, peak release occurs in a short period of time (about three hours), whereas muscle cell growth. To evaluate this parameter, smooth muscle cells at a density of 5,000 cells/cm$^2$ are seeded onto control tissue culture surface and testing matrices. Data are presented in Table 8. Cell growth curves are presented in FIG. 15.

TABLE 8

Comparison of Inhibition of Growth of Smooth Muscle Cells Using
Collagen Matrices Saturated with Actinomycin D and Rapamycin

| | Number of Cells | | |
|---|---|---|---|
| Days in Culture | Control | Collagen + Actinomycin D | Collagen + Rapamycin |
| 0 | 5000 | 5000 | 5000 |
| 1 | 6430 ± 20.4 | 5230 ± 16.8 | 4800 ± 9.5 |
| 2 | 10240 ± 27.1 | 7350 ± 19.5 | 5040 ± 11.2 |
| 3 | 16340 ± 30.12 | 9400 ± 13.2 | 6230 ± 13.4 |
| 4 | 27100 ± 25.4 | 14280 ± 17.6 | 7400 ± 15.1 |
| 5 | 38450 ± 22.6 | 23540 ± 17.8 | 8000 ± 17.8 |
| 6 | 40000 ± 20.7 | 29300 ± 19.4 | 8550 ± 13.9 |
| 7 | 40100 ± 20.5 | 32090 ± 32.1 | 8500 ± 14.4 |

Actinomycin D is quickly released from the drug matrix and suppresses cell growth for only a short period of time. A change of media removes soluble actinomycin, and after several washes, no antibiotic is present in the media or in the matrix. As a result, cells start proliferating as usual. Rapamycin is slowly released. Because of this slow, gradual release of rapamycin (sirolimus), suppression of cell growth continued throughout the observation period.

Example 9

Effect of Ratio of Matrix to Media on Antiproliferative Activity

Two different types of matrices, collagen and fibrin combined with antiproliferative agents, alone or in combination, along with vitamin K, are added to the cell culture medium in different ratios. Cells are seeded at the same density, and on day 5, numbers of viable cells are measured by Alamar blue assay. Data are presented in Table 9.

TABLE 9

| | Inhibition of Cell Growth (%) | | | | |
|---|---|---|---|---|---|
| Matrix to Media Ratio | Collagen + Rapamycin | Collagen + Rapamycin + Taxol | Collagen + Rapamycin + Vitamin K | Fibrin + Rapamycin | Fibrin + Rapamycin + Taxol |
| 1:400 | 5 | 4 | 8 | 3 | 2 |
| 1:200 | 25 | 27 | 34 | 21 | 19 |
| 1:100 | 54 | 50 | 77 | 56 | 55 |
| 1:50 | 73 | 76 | 99 | 79 | 78 |
| 1:25 | 88 | 88 | 99 | 79 | 84 |
| 1:12.5 | 95 | 99 | 99 | 98 | 96 |
| 1:6.25 | 95 | 99 | 99 | 100 | 98 |

Example 10

Antiproliferative Effect of Combination of Rapamycin and Heparin Combined to a Collagen Matrix Antiproliferative effects of different components combined within a matrix may exhibit a synergy. A combination of dispersed rapamycin and soluble and immobilized heparin are used. To immobilize heparin, 5 ml of chilled heparin solution at a concentration of 1-10 mg/ml, preferably 5 mg/ml, is mixed with 5-20 ml, preferably 11.4 ml, of acrylic acid chloranhydride at the rate of approximately 1 µl/min, preferably 2.5 µl/min. After addition, the mixture is agitated for 30 minutes at a temperature of 4-8° C. The heparinized collagen is extensively washed with sodium phosphate buffered saline at pH 7.4. A colorimetric assay with Eosin A is used to determine the concentration of heparin immobilized on matrix. Using this method, between 0.01-0.1 mg/cm$^2$ may be covalently linked to the matrix.

Such a formulation combined with rapamycin has inhibitory effect on smooth muscle cell growth in culture if added in the form of suspension into the media at a ratio of 1:100, whereas individual forms have lesser effects—ratio of 1:25 for heparin alone to 1:65 for dispersed rapamycin. Each of these drugs can inhibit restenosis by different mechanisms. Hence, it is reasonable to expect synergistic effect when using the drugs in combination. Heparin can also be used in matrix saturated form in combination with antiproliferatives.

Example 11

Rate of Release of Dexamethasone in Collagen Matrix

Sustained local delivery of dexamethasone in combination with rapamycin (sirolimus) or other antiproliferative agents can be used to simultaneously inhibit restenosis as well as inflammatory reactions. Twenty percent (w/w) collagen slurry is prepared, to which a 2% (w/w) suspension of dexamethasone is added. This mixture is sprayed on to a plastic surface to form the film. The final thickness of the film ranged from 1.92-2.14 mm (mean 2 mm). This sheet is flexible and mechanically stable. The kinetics of dexamethasone elution from the matrix (collagen plus rapamycin) were characterized in an in vitro system. Fifteen-millimeter diameter sheets were placed in the wells and immersed in 2.5 ml of phosphate buffered solution. At time points ranging from 1-7 days, concentrations of dexamethasone in aliquots of elution buffer were measured by spectrophotometry. Chemical stability of the dexamethasone through the sheet formation, drying storage, and elution process was confirmed by HPLC. Cumulative in vitro elution of dexamethasone is shown in Table 10.

TABLE 10

Cumulative In-Vitro Elution of Dexamethasone from A Collagen Matrix

| Time (days) | Eluted Dexamethasone Mass (µg) |
|---|---|
| 0 | 0 |
| 1 | 211 ± 23 |
| 2 | 489 ± 31 |
| 3 | 605 ± 42 |
| 4 | 672 ± 38 |
| 5 | 725 ± 21 |
| 6 | 733 ± 18 |
| 7 | 745 ± 13 |

More than 50% of the dexamethasone elution occurred within the first three days, with a leveling off of the elution curves after six days. Dexamethasone can prevent a severe inflammatory response, which is maximal during this time period, and can act synergistically with rapamycin (sirolimus) to reduce restenosis. In contrast to a dexamethasone eluting stent, perivascular delivery does not inhibit endothelial cell regeneration and acts directly on fibroblasts and smooth muscle cells.

Example 12

Rate of Release of Heparin in Collagen Matrix

Combining macro- and micro-porosity may increase capacity of the device. Collagen and fibrin matrices were mixed to obtain such a combination. In addition, good mechanical characteristics of collagen improved stability of fibrin. To prepare fibrin-rapamycin loaded matrix (rapamycin density of 150 μg/cm$^2$), compositions disclosed in Tables 6 and 7 were used. After formation of a first dry layer of fibrin, a second layer of collagen, rapamycin (sirolimus), and heparin was formed as described in Example 4 (rapamycin density of 128 μg/cm$^2$, heparin density of 5,000 U/cm$^2$).

The collagen fibrin sheaths loaded with medicine (thickness 2 mm) were formed as tubular structures and externally crosslinked using high a concentration of glutaraldehyde (25%) for one minute. After drying, the spiral form of the sleeve shown in FIG. 4 was prepared. This sleeve was made planar on ten occasions, and the spiral shape was restored each time. The rapamycin (sirolimus) capacity of the final sleeve was 143 μg/cm$^2$. In vitro elution of heparin continues for seven days. Heparin concentration was measured as in Example 10. Buffer for the dilution was replenished each day. The data are shown in Table 11.

TABLE 11

Elution Profile of Heparin from A Collagen Matrix Combined with Rapamycin and Heparin

| Time (days) | Eluted Heparin Mass (u/ml) |
|---|---|
| 0 | 0 |
| 1 | 341 |
| 2 | 275 |
| 3 | 188 |
| 4 | 103 |
| 5 | 57 |
| 6 | 24 |
| 7 | 8 |

Heparin effectively inhibits smooth muscle cell proliferation at a concentration of about 100 u/ml. In this example, heparin can significantly inhibit smooth muscle cell proliferation for at least four days. In addition, diffusion of heparin from the sleeve can prevent thrombotic events on the inner surface of the shunt and damaged vessel wall for longer periods of time. Furthermore, the concentration of soluble heparin can be increased up to 20,000 U/cm$^2$ without changing the mechanical characteristics of the matrix. Therefore, anti-smooth muscle cell proliferation as well as antithrombotic effect can be prolonged.

Examples 13 and 14

Comparison of In Vitro Effect of Paclitaxel, Rapamycin, and Tacrolimus on Human Smooth Muscle and Endothelial Cells Human smooth muscle cells and endothelial cells (Cambrex Corp., formerly Clonetics Corp., East Rutherford, N.J.) were seeded (100,000 cells) in 24-well plates overnight. Both cell types were grown and maintained in Opti-MEM (Invitrogen, Carlsbad, Calif.) and 5% fetal bovine serum at 37° C. in a 5% carbon dioxide and 95% atmospheric air. Cells were exposed to a range of concentrations of rapamycin (10-100 nM), paclitaxel (0.1-10 mM), and tacrolimus (10-100 nM). Each cell type was allowed to grow for 24 hours, last four hours in the presence of [$^3$H]-thymidine.

Figure 16:
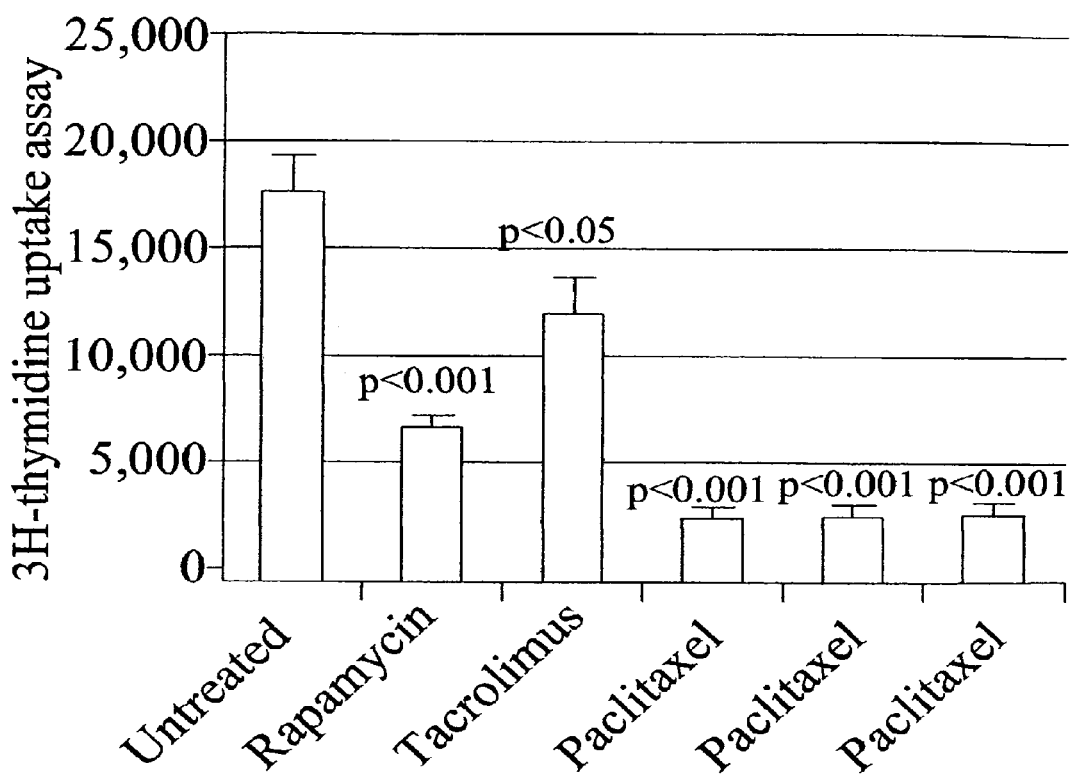
FIG. 16 is a comparison of the effect of paclitaxel (3 doses), rapamycin (sirolimus), and tacrolimus on human smooth muscle cells.
Figure 17:
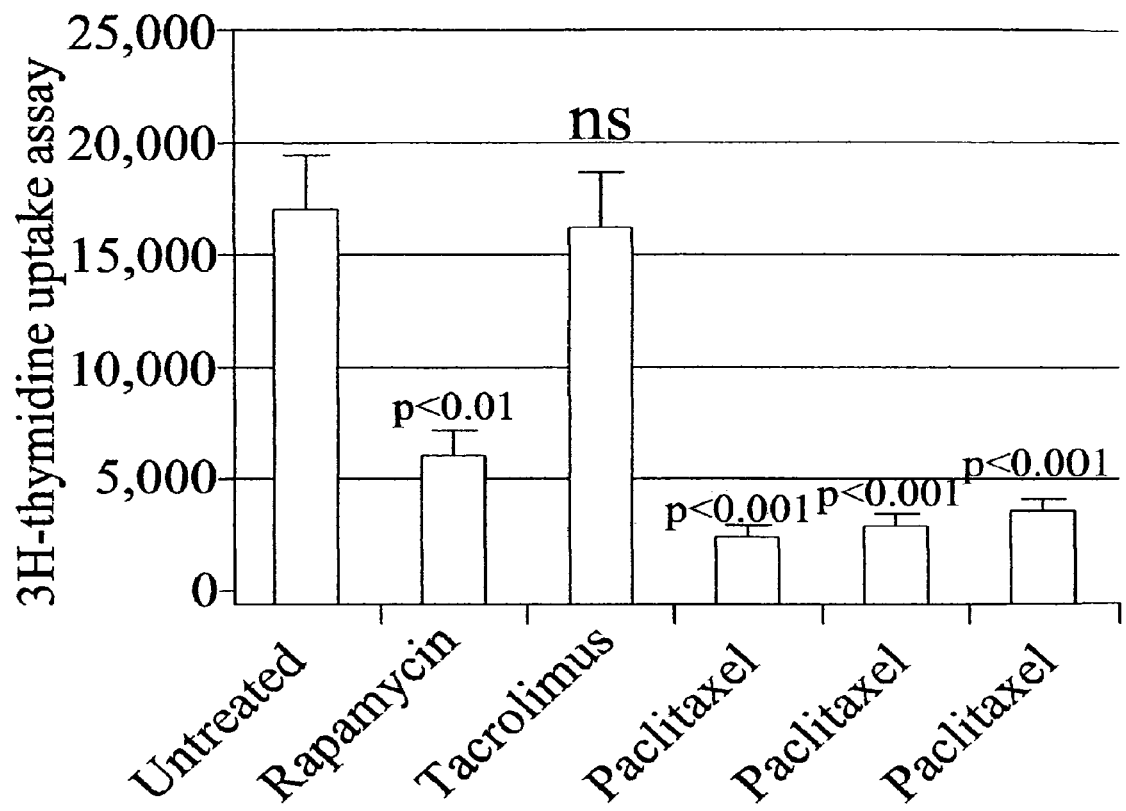
FIG. 17 is a comparison of the effect of paclitaxel (3 doses), rapamycin (sirolimus), and tacrolimus on human endothelial cells.

Proliferation of cells was quantified as new DNA synthesis using [$^3$H]-thymidine uptake assay. After 72 hours of culture, cells were washed twice with cold phosphate buffered saline (PBS), and 1 ml of methanol was added to the contents of each well. The plates were kept at 4° C. for 60 minutes, the cells then washed once with cold PBS, and 500 μl of 0.2 m M NaOH was added to each well, and the plates kept at 4° C. for 30 minutes. The contents of each well were transferred into scintillation vials, and liquid scintillation fluid was added to quantify radioactivity using a liquid scintillation counter and the results expressed as counts per minute. Results are shown in Tables 12 and 13 and corresponding FIGS. 16 and 17, respectively.

TABLE 12

Comparison of Effect of Paclitaxel (3 doses), Rapamycin, and Tacrolimus on Human Smooth Muscle Cells

| | [$^3$H]-Thymidine Uptake Assay, Mean ± SD | p |
|---|---|---|
| Control (untreated) | 17434 ± 1822 | |
| Paclitaxel | 2421 ± 206 | <0.001 |
| Paclitaxel | 2527 ± 195 | <0.001 |
| Paclitaxel | 2710 ± 162 | <0.001 |
| Rapamycin | 6498 ± 245 | <0.01 |
| Tacrolimus | 11995 ± 1850 | <0.05 |

TABLE 13

Comparison of Effect of Paclitaxel (3 doses), Rapamycin, and Tacrolimus on Human Endothelial Cells

| | [$^3$H]-Thymidine Uptake Assay, Mean ± SD | p |
|---|---|---|
| Control (untreated) | 16342 ± 3039 | |
| Paclitaxel | 2222 ± 228 | <0.001 |
| Paclitaxel | 2648 ± 248 | <0.001 |
| Paclitaxel | 3459 ± 272 | <0.001 |
| Rapamycin | 5787 ± 1323 | <0.01 |
| Tacrolimus | 16073 ± 3008 | ns |

Rapamycin (sirolimus) and paclitaxel inhibit proliferation (new DNA synthesis) of both human smooth muscle and endothelial cells. Tacrolimus appears to preferentially inhibit new DNA synthesis in human smooth muscle cells, sparing endothelial cells. This differential effect may be extremely important and can be beneficially exploited if tacrolimus were to be used for inhibition of smooth muscle cell proliferation.

Example 15

Animal Studies

A proof of principle study was performed using a porcine model. A total of six pigs were studied, two as controls and four as treated. A 6 mm PTFE vascular graft was anastomosed between the carotid artery on one side and the contralateral jugular vein. This created an arterio-venous (AV) loop that is similar in construction to the human hemodialysis access loop. A collagen sleeve combined with a known dose of rapamycin (approximately 500 µg/cm$^2$) was placed around the distal end of the PTFE vascular graft just proximal to the venous anastomosis in the treated group.

After 30 days, an angiogram was performed to demonstrate vessel and graft patency. The animals were euthanized and the relevant segments dissected. The inhibitory effect of rapamycin (sirolimus) on cell cycle progression is believed to be by induction of cyclin inhibitors. Hence, expression of p21 will increase in tissues obtained from rapamycin (sirolimus) treated animals but not from controls. In other words, the presence of p21 confirms that the observed effect is attributable to rapamycin (sirolimus). Tissues from treated and untreated animals were obtained, and RNA was prepared and reverse transcribed to cDNA, which was amplified for housekeeping gene b-actin and p21 by PCR.

Figure 18A:
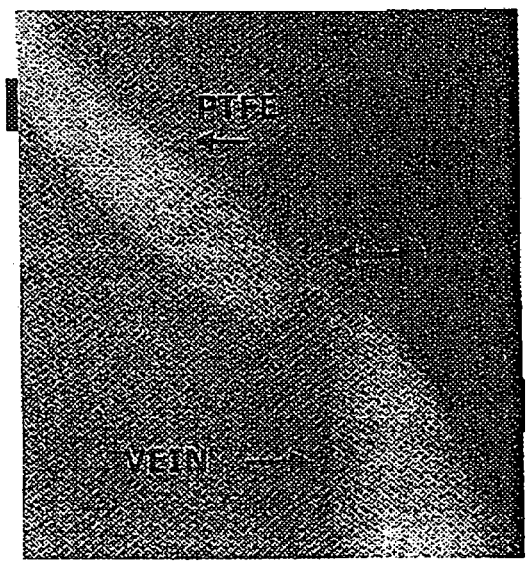
Figure 18B:
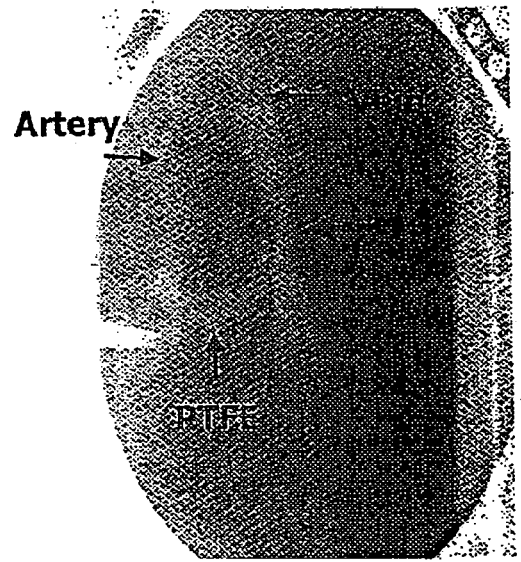
Figure 19A:
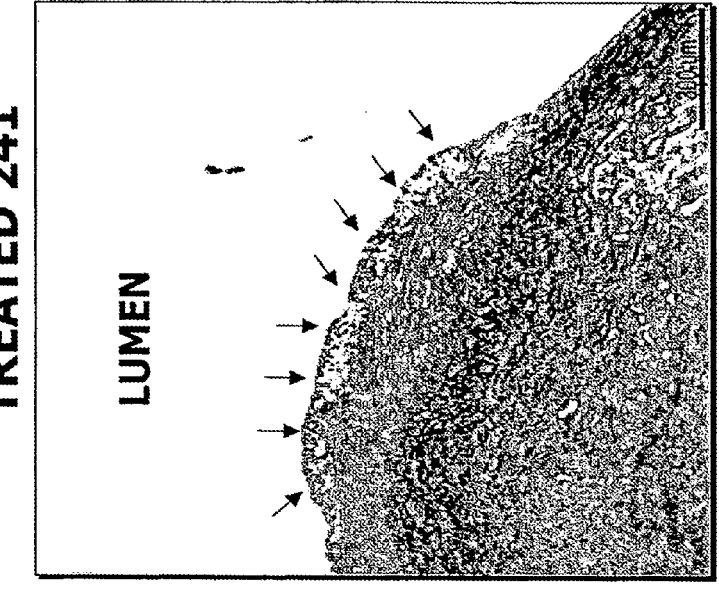
Figure 19B:
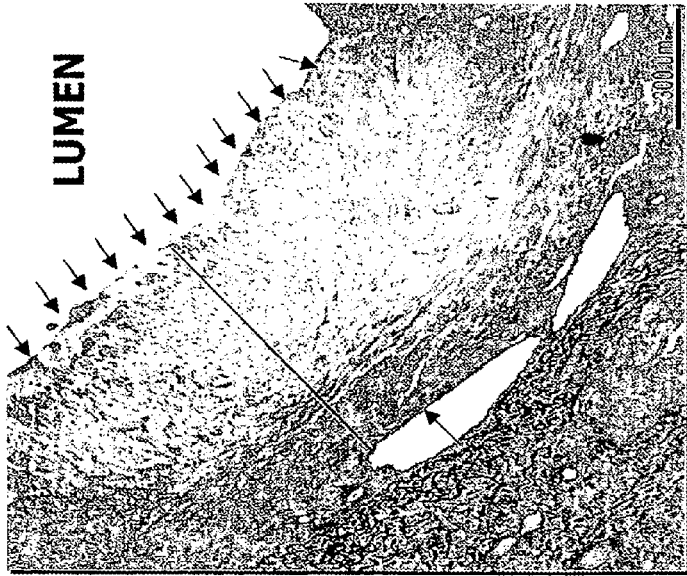

Both controls had luminal narrowing caused by severe neointimal hyperplasia at the site of venous anastomosis (FIGS. 18A and 19A). All four treated animals had significantly higher luminal patency of the vein and the graft, with minimal to absent neointimal hyperplasia (FIGS. 18B and 19B). Expression of p21 mRNA was observed in venous tissue at the perianastamotic site obtained from rapamycin (sirolimus) treated animals (FIG. 20) but not from controls. This demonstrates that the rapamycin (sirolimus) contained in the sleeve matrix was responsible for the reduction of neointimal hyperplasia by inhibiting cellular proliferation.

Example 16

A 6.0 mm PTFE graft was anastamosed between the carotid artery and the jugular vein. A total of 19 animals were utilized for this study. At the time of surgical construction of the A-V graft, collagen matrix with or without the drug was implanted at the site of venous anastomosis. Five animals served as controls (Group A, plain collagen matrix, no drug); the remaining 14 animals received treatment. They were divided into two equal groups (B and C) of seven animals each. One set of treated animals received Dose 1 (Group B, total dose 500 µg) of rapamycin and the other set received Dose 2 (Group C, total dose 2000 µg of rapamycin). Salient features of the protocol are summarized in Table 20. Animals (n=13) were euthanized after 1 month. Tissues were formalin fixed and sent for histology.

Histological assessment of graft explants was performed by examining the following components: (1) the venous anastamotic site; (a) luminal and (b) adventitial surfaces, (2) the venous end away from the anastomosis; (c) luminal and (d) adventitial surfaces and (3) the PTFE graft; (e) luminal and (f) abluminal surfaces away from the anastamosis (FIG. 2). The following parameters were evaluated: intimal thickening, inflammation, thrombus, fibrosis, hemorrhage/fibrin and calcification or any other pathological changes observed. Histological evaluation was scored on a 0 through 4 scale, where 0=no significant change, 1=minimal, 2=mild, 3=moderate and 4=severe.

P-values obtained from semiquantitative analysis of histological findings using ANOVA (t-test unpaired).

TABLE 14

| Group | Acute Inflammation P-Value | Chronic Inflammation P-Value | Fibrosis P-Value | Collagen Degradation P-Value |
|---|---|---|---|---|
| Control vs. Dose 1 | 0.1259 | 0.5833 | 0.0149 | 0.0665 |
| Control vs. Dose 2 | 0.3071 | 0.4445 | 0.0298 | 0.0083 |
| Dose 1 vs. Dose 2 | 0.5247 | 0.8317 | 0.6485 | 0.3726 |

There was no statistical difference in the degree of inflammation between treated and controls. There was a significant difference in the degree of fibrosis when comparing the control group vs. treatment groups, but no significant differences when comparing the two dosages together. Collagen degradation was significant in Dose 2 when compared with the control group but insignificant when compared to Dose 1.

Example 17

A total of 4 pigs will be used, 2 controls and 2 treated. A 6 mm PTFE vascular graft will be anastomosed between the carotid artery and the jugular vein, and this creates an arteriovenous (AV) loop that is similar in construction to the human hemodialysis access loop. A collagen sleeve combined with a known dose of everolimus will be placed around the distal end of the PTFE vascular graft just proximal to the venous anastomosis in the treated group.

After 30 days an angiogram will done to demonstrate vessel and graft patency, the animals will be euthanized and the relevant segments dissected. Tissue samples will be sent for histology and histomorphometry.

Like we have demonstrated with rapamycin, we expect to see reduction in stenosis at the site of venous anastomosis in treated compared to controls. This will be confirmed on angiograms as well by amount of neointimal thickness on histomorphometry.

Those skilled in the art will appreciate that numerous other embodiments and modifications are contemplated by the present invention. The above description of embodiments is merely illustrative and not intended to limit the scope of the present invention. The patents, literature, and references cited herein are incorporated by reference in their entireties.

What is claimed is:

1. A method of treating a site of vascular compromise in a target vessel to seal a puncture or opening, and treat, suppress or prevent a tissue response at such site resulting from the sealing of the puncture or opening, comprising the steps of:
combining a tissue response regulating amount of rapamycin and a hemostatic material comprising a sheet of collagen, wherein the sheet of collagen is either impregnated, absorbed, adsorbed, saturated, dispersed or immobilized with rapamycin in an amount of about 0.2 µg/cm$^2$ to 2.0 mg/cm$^2$ of the collagen and has an effective pore size from about 0.001 to 100 µm, and wherein the hemostatic device is configured to be perivascularly applied around the outer circumferential surface of the target vessel at the site of the vascular compromise; and
applying the combination perivascularly to the target vessel at the site of vascular compromise such that the combination is placed over and around an outer circumferential surface of the target vessel, seals the puncture or opening, and elutes the rapamycin to the target vessel over the substantial length of the hemostatic device.

2. The method of claim 1, wherein the collagen is Type I Bovine collagen.

3. The method of claim 1, wherein the collagen is selected from the group consisting of Type I, Type II, Type III, Type IV, Type XI, and mixtures thereof.

4. The method of claim 1, wherein the hemostatic material is selected from the group consisting of collagen, fibrin, chitosan and mixtures thereof.

5. The method according to any one of claims 2-4, wherein the hemostatic material is biodegradable.

6. The method of claim 1, wherein the rapamycin is present in an amount of about 0.001 microgram to about 200 micrograms per mg weight of the combination and wherein the material is collagen.

7. The method of claim 1, wherein the material is a sheet of collagen that is either impregnated, absorbed, adsorbed, saturated, dispersed or immobilized with rapamycin in an amount of about 120 µg/cm$^2$ of the collagen.

8. The method of claim 1, wherein the material is collagen which, when in dry form, is a sheet that is 0.3 to 3.0 mm thick.

9. The method of claim 1, wherein the rapamycin is present in an amount of about 0.2 microgram to about 100 mg per mg weight of the device or material.

10. The method of claim 1, wherein the rapamycin is present in an amount of about 5 µg/cm$^2$.

11. The method of claim 1, wherein the combination further comprises a therapeutic agent selected from the group consisting of actinomycin D, cyclosporin A, methotrexate, paclitaxel, heparine, dexamethasone, everolimus, and tetracycline.

12. The method of claim 11, wherein the therapeutic agent is present in an amount of about 5 µg/cm$^2$.

13. The method of claim 1, wherein the rapamycin is present in an amount of about 120±5 µg/cm$^2$.

14. The method of claim 1, wherein the rapamycin is present in an amount of about 60±4 µg/cm$^2$.

15. The method of claim 1, wherein the rapamycin is present in an amount of about 30±3 µg/cm$^2$.

16. The method of claim 1, wherein the rapamycin is present in an amount of about 500 µg/cm$^2$.

17. The method of claim 1, wherein the rapamycin is present in an amount of about 2000 µg/cm$^2$.

18. The method of claim 1, wherein the rapamycin is present in an amount of about 50 µg/cm$^2$ to 2 mg/cm$^2$.

19. A method of treating a site of vascular compromise in a target vessel to seal a puncture or opening, and treat, suppress or prevent a tissue response at such site resulting from the sealing of the puncture or opening, comprising the steps of:

combining a tissue response regulating amount of rapamycin as the sole therapeutically active agent and collagen, wherein the collagen is in the form of a sheet having an effective pore size from about 0.001 to 100 µm; and applying the combination perivascularly to the target vessel at the site of vascular compromise such that the combination is placed over and around an outer circumferential surface of the target vessel, seals the puncture or opening, and elutes the rapamycin to the target vessel over the substantial length of the applied rapamycin and collagen combination.

20. The method of claim 19, wherein the rapamycin is present in an amount of about 0.001 microgram to about 200 micrograms per mg weight of the combination.

21. The method of claim 19, wherein the material is a sheet of collagen that is either impregnated, absorbed, adsorbed, saturated, dispersed or immobilized with rapamycin.

22. The method of claim 19, wherein the sheet of collagen is either impregnated, absorbed, adsorbed, saturated, dispersed or immobilized with rapamycin in an amount of about 0.2 µg/cm$^2$ to 2.0 mg/cm$^2$ of the collagen.

23. The method of claim 19, wherein the sheet of collagen is either impregnated, absorbed, adsorbed, saturated, dispersed or immobilized with rapamycin in an amount of about 120 µg/cm$^2$ of the collagen.

24. The method of claim 19, wherein the collagen which, when in dry form, is a sheet that is 0.3 to 3.0 mm thick.

25. The method of claim 19, wherein the rapamycin is present in an amount of about 0.2 microgram to about 100 mg per mg weight of the device or material.

26. The method of claim 19, wherein the rapamycin is present in an amount of about 5 µg/cm$^2$.

27. The method of claim 19, wherein the rapamycin is present in an amount of about 120±5 µg/cm$^2$.

28. The method of claim 19, wherein the rapamycin is present in an amount of about 60±4 µg/cm$^2$.

29. The method of claim 19, wherein the rapamycin is present in an amount of about 30±3 µg/cm$^2$.

30. The method of claim 19, wherein the rapamycin is present in an amount of about 500 µg/cm$^2$.

31. The method of claim 19, wherein the rapamycin is present in an amount of about 2000 µg/cm$^2$.

32. The method of claim 19, wherein the rapamycin is present in an amount of about 50 µg/cm$^2$ to 2 mg/cm$^2$.

33. The method of claim 19, wherein the rapamycin is present in an amount of about 50 µg/cm$^2$ to 10 mg/cm$^2$.

* * * * *